(12) United States Patent
Lualdi

(10) Patent No.: US 8,012,199 B2
(45) Date of Patent: Sep. 6, 2011

(54) ENDOLUMENAL DEVICE FOR DELIVERING AND DEPLOYING AN ENDOLUMENAL EXPANDABLE PROSTHESIS

(76) Inventor: Alessandro Lualdi, Milan (IT)

( * ) Notice: Subject to any disclaimer, the term of this patent is extended or adjusted under 35 U.S.C. 154(b) by 286 days.

(21) Appl. No.: 12/471,281

(22) Filed: May 22, 2009

(65) Prior Publication Data

US 2009/0299457 A1 Dec. 3, 2009

Related U.S. Application Data

(62) Division of application No. 10/204,251, filed as application No. PCT/EP00/12964 on Dec. 19, 2000, now Pat. No. 7,540,879.

(30) Foreign Application Priority Data

Feb. 18, 2000 (EP) .................................. 00200572

(51) Int. Cl.
*A61F 2/06* (2006.01)
(52) U.S. Cl. ...................................... 623/1.35; 623/1.11
(58) Field of Classification Search .................. 623/1.11, 623/1.12, 1.35; 606/108
See application file for complete search history.

(56) References Cited

U.S. PATENT DOCUMENTS

| | | | |
|---|---|---|---|
| 5,295,995 A | 3/1994 | Kleiman | |
| 5,336,178 A | 8/1994 | Kaplan et al. | |
| 5,336,184 A | 8/1994 | Teirstein | |
| 5,413,557 A | 5/1995 | Solar | |
| 5,549,553 A | 8/1996 | Ressemann et al. | |
| 5,669,880 A | 9/1997 | Solar | |
| 5,795,331 A | 8/1998 | Cragg et al. | |
| 5,980,484 A | 11/1999 | Ressemann et al. | |
| 6,007,517 A | 12/1999 | Anderson | |
| 6,099,497 A | 8/2000 | Adams et al. | |
| 6,221,080 B1 | 4/2001 | Power | |
| 6,436,104 B2 | 8/2002 | Hojeibane | |
| 6,682,556 B1 | 1/2004 | Ischinger | |
| 7,540,879 B2 | 6/2009 | Lualdi | |
| 2001/0004706 A1 | 6/2001 | Hojeibane | |
| 2001/0029396 A1 | 10/2001 | Wilson et al. | |
| 2005/0222666 A1 | 10/2005 | Lualdi | |

FOREIGN PATENT DOCUMENTS

EP 0891751 1/1999

(Continued)

OTHER PUBLICATIONS

International Search Report of PCT Application No. PCT/EP00/12964 mailed Jul. 26, 2001 in 6 pages.

(Continued)

*Primary Examiner* — Julian W Woo
(74) *Attorney, Agent, or Firm* — Knobbe, Martens, Olson & Bear LLP

(57) ABSTRACT

An endolumenal device (1) for delivering and deploying an endolumenal expandable prosthesis (6) at a bifurcation provided with a main conduit and at least a secondary conduit, comprises an elongated body (2) having a proximal end portion (4) and a distal end portion (3); the distal end portion (3) comprising expansion means (5) having a longitudinally extended active portion removably engageable with the prosthesis (6). Said active portion of the expansion means is longitudinally associated to the body in order to expand said prosthesis eccentrically from one side with respect to the body, in order to leave free from said expanded active portion the other side of the body. The device further is provided with guidewire tracking means (11).

2 Claims, 24 Drawing Sheets

FOREIGN PATENT DOCUMENTS

| | | |
|---|---|---|
| EP | 0897700 A1 | 2/1999 |
| EP | 0897700 B1 | 7/2002 |
| JP | 3004480 | 8/1993 |
| RU | 2108764 | 4/1998 |
| RU | 2121317 | 11/1998 |
| WO | WO 95/01202 | 1/1995 |
| WO | WO 96/34580 | 11/1996 |
| WO | WO 97/04829 | 2/1997 |
| WO | WO 97/45073 | 12/1997 |
| WO | WO 98/36709 | 8/1998 |
| WO | WO 99/03426 | 1/1999 |
| WO | WO 99/15103 | 4/1999 |
| WO | WO 99/44539 | 9/1999 |
| WO | WO 00/74595 | 12/2000 |
| WO | WO 01/60284 | 8/2001 |
| WO | WO 01/78621 | 10/2001 |

OTHER PUBLICATIONS

International Search Report of PCT Application No. PCT/IB03/01178 mailed Aug. 4, 2003 in 7 pages.

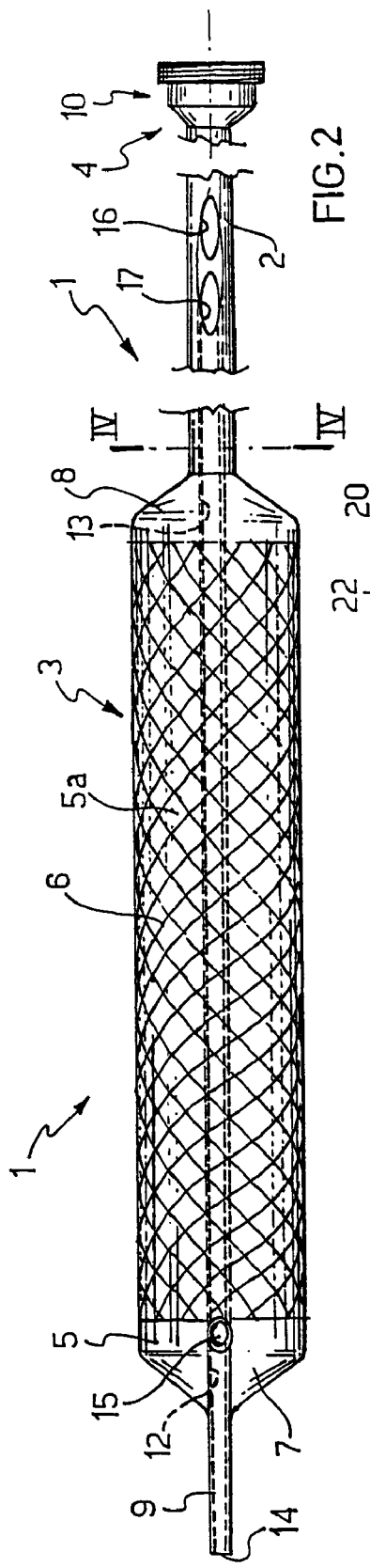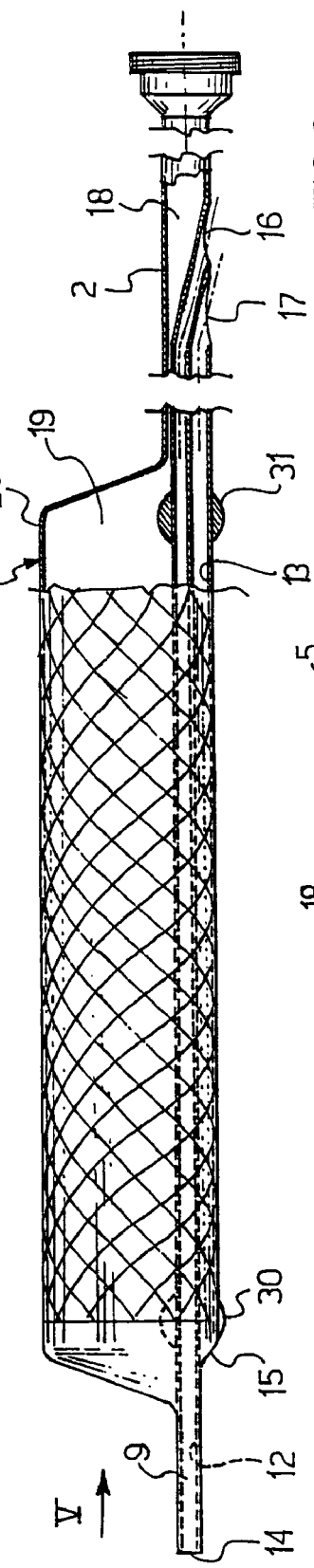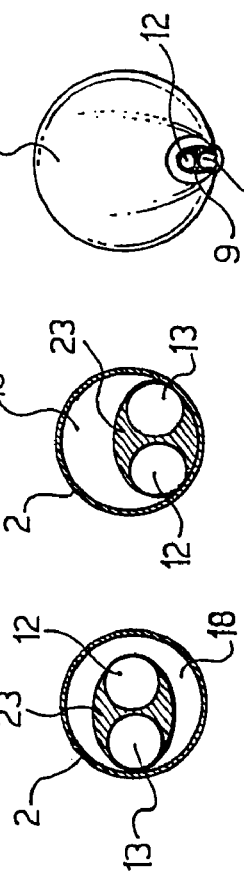

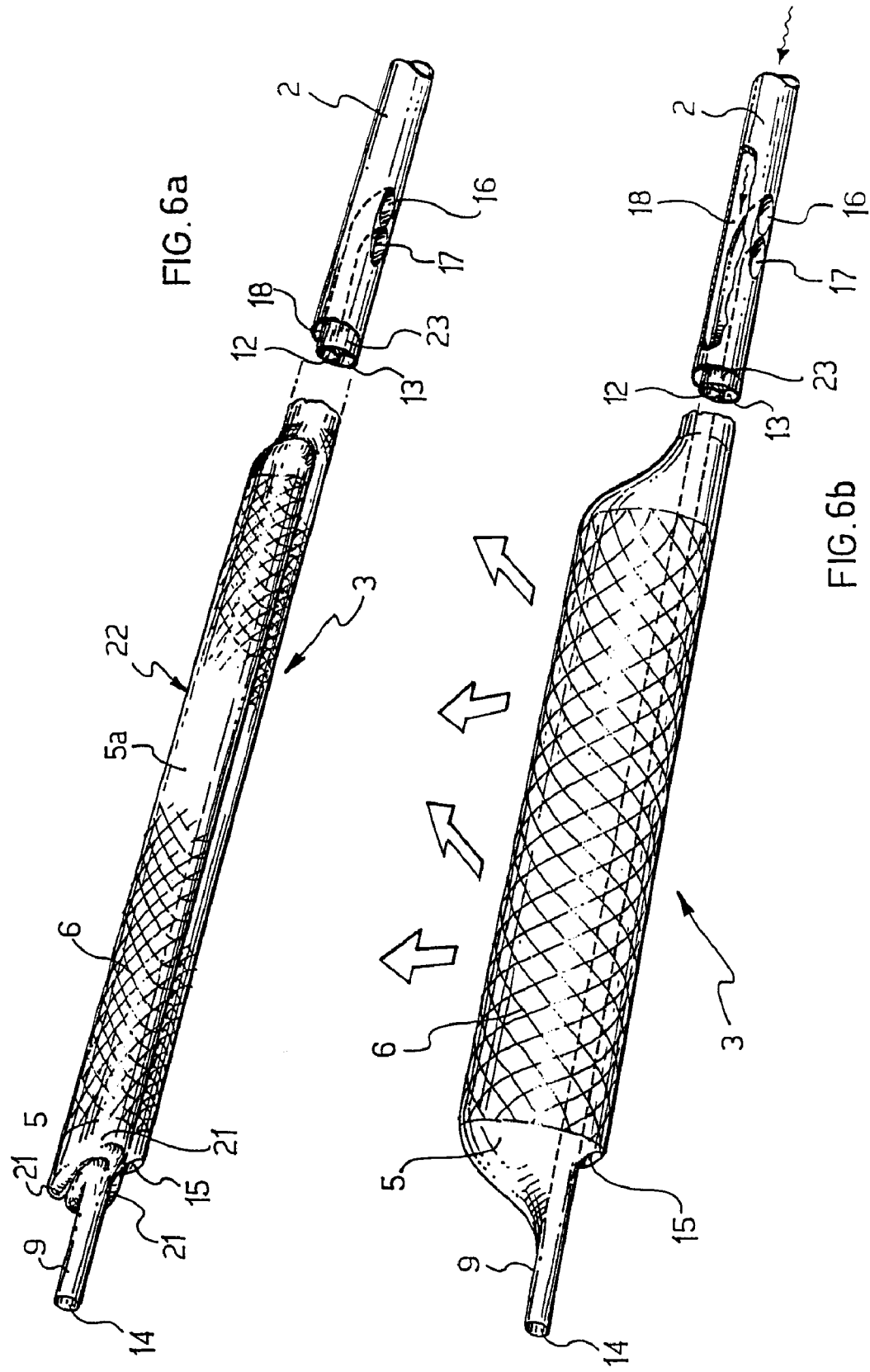

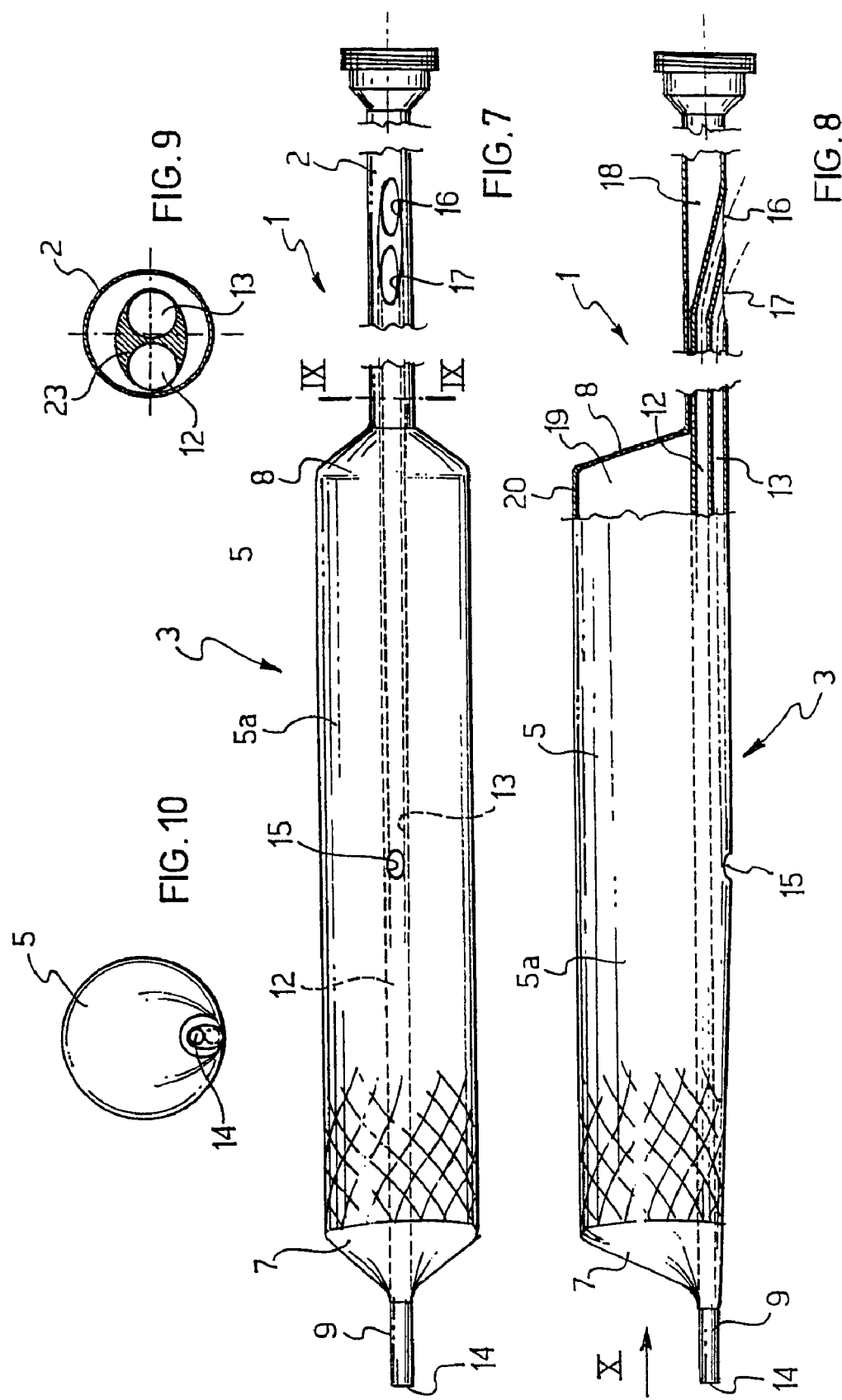

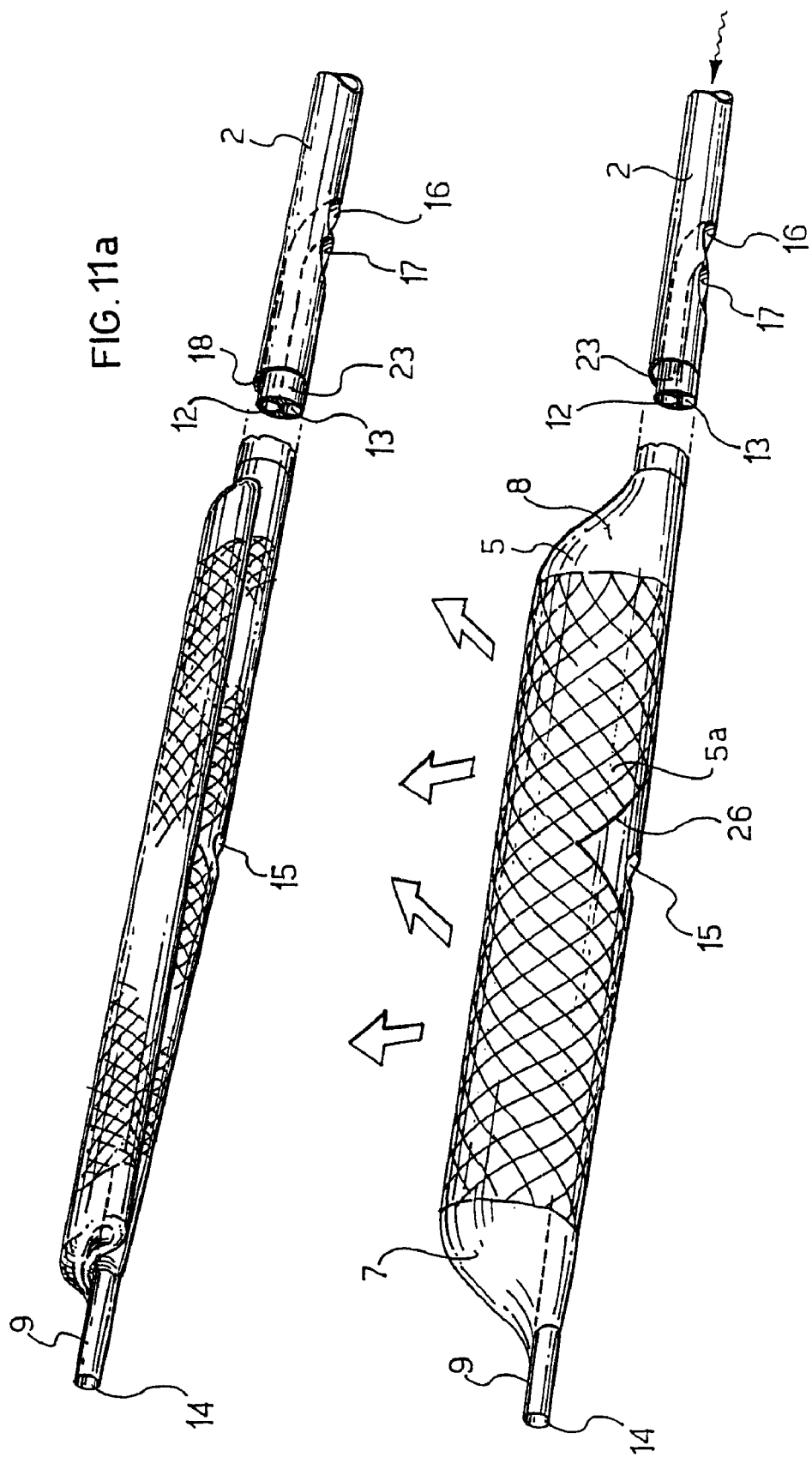

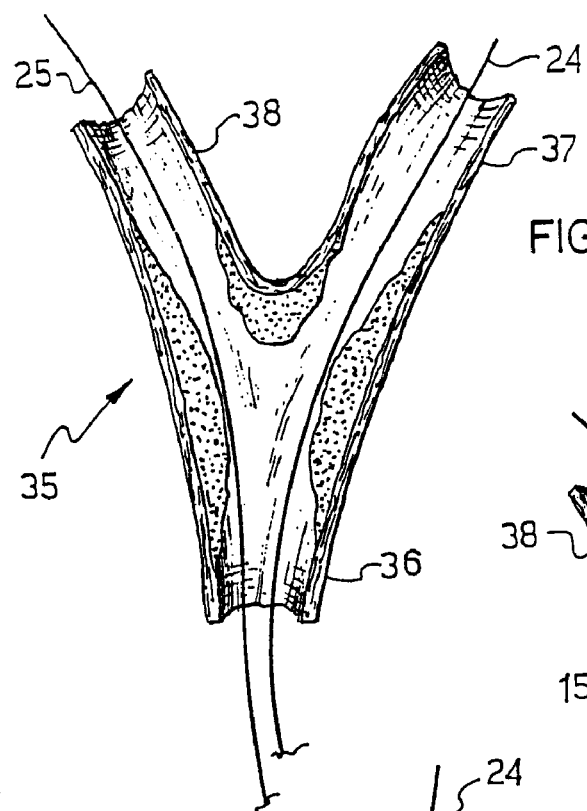
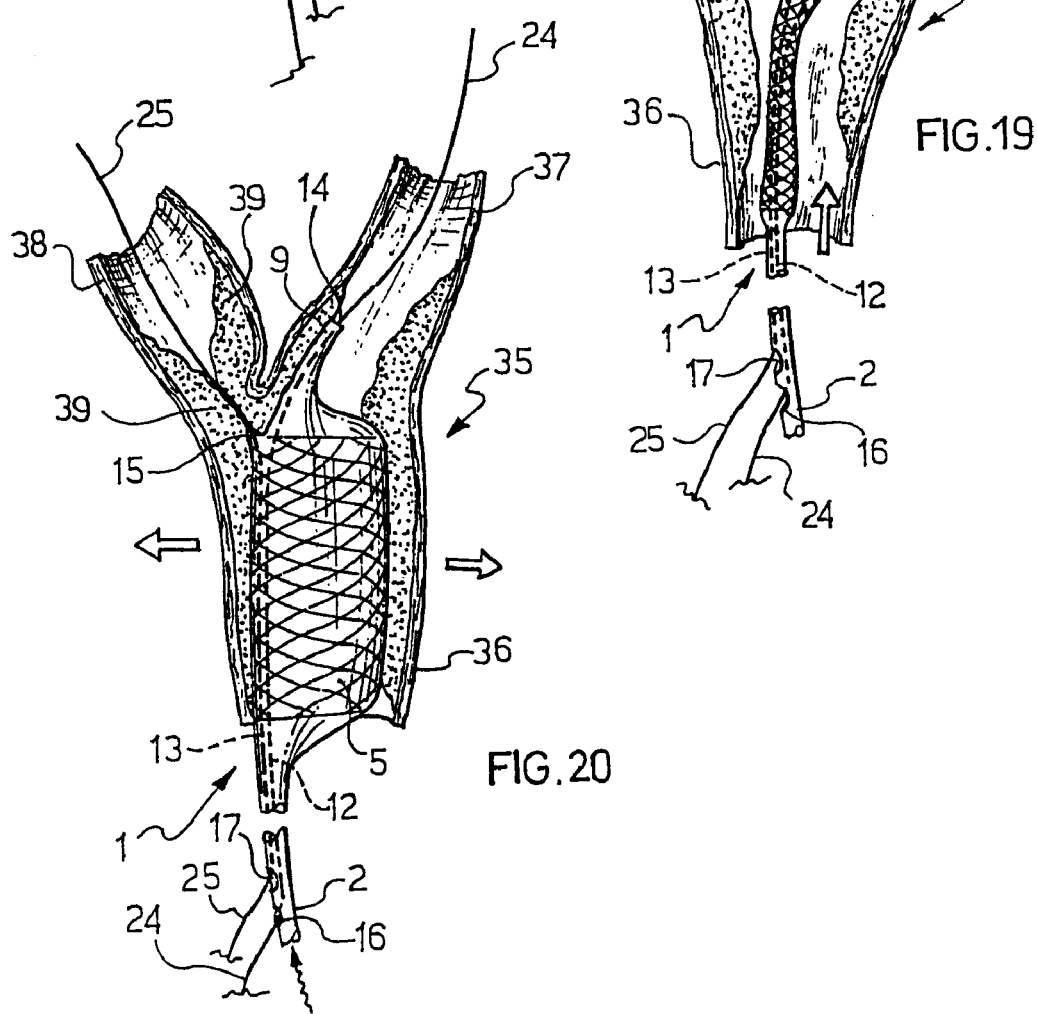
FIG. 18
FIG. 19
FIG. 20

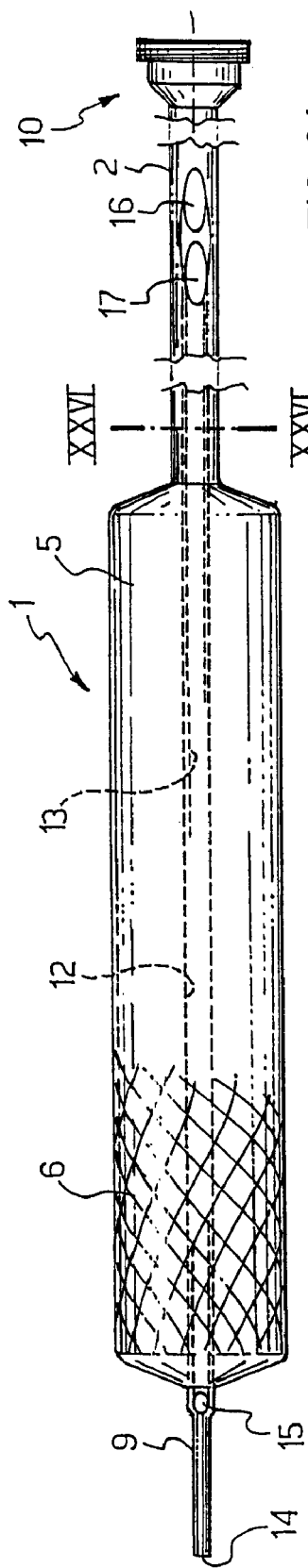
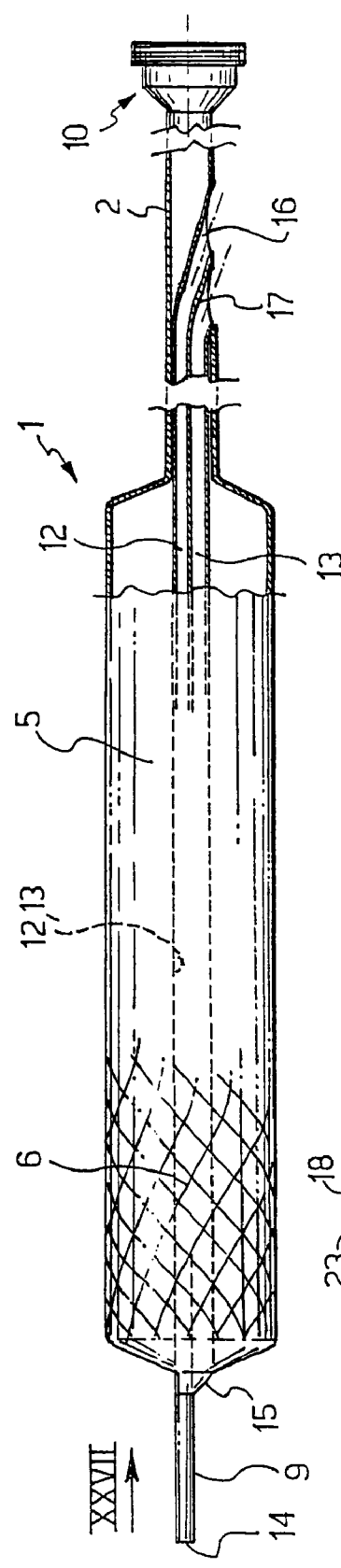
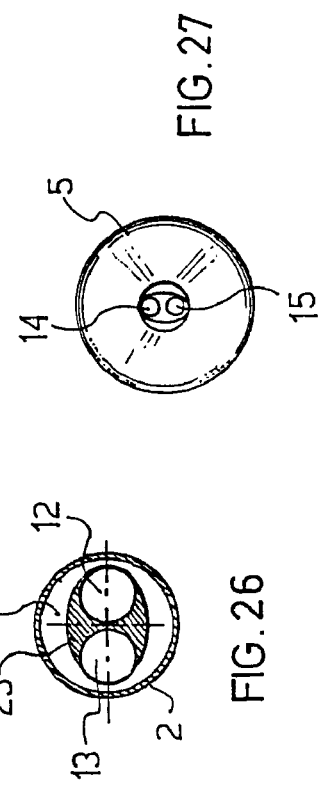
FIG. 24
FIG. 25
FIG. 27
FIG. 26

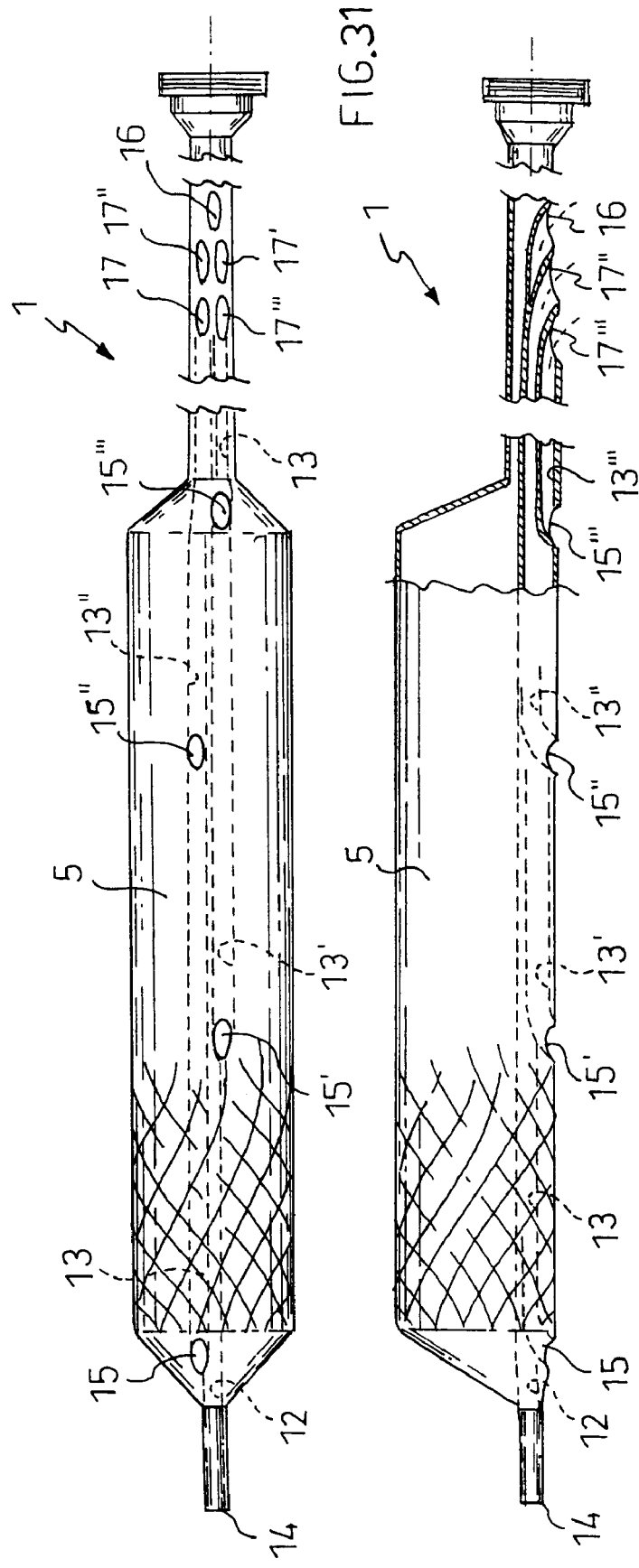

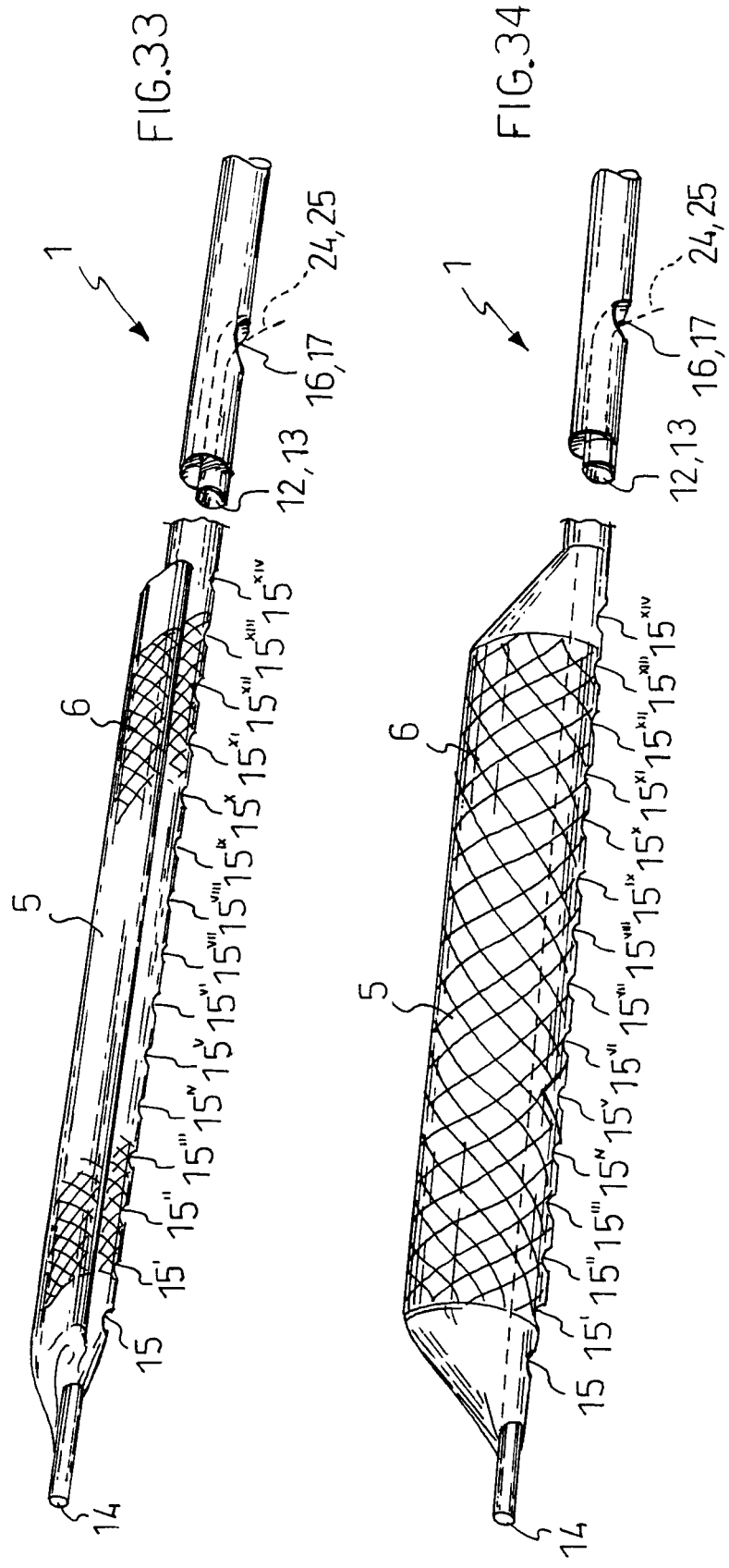

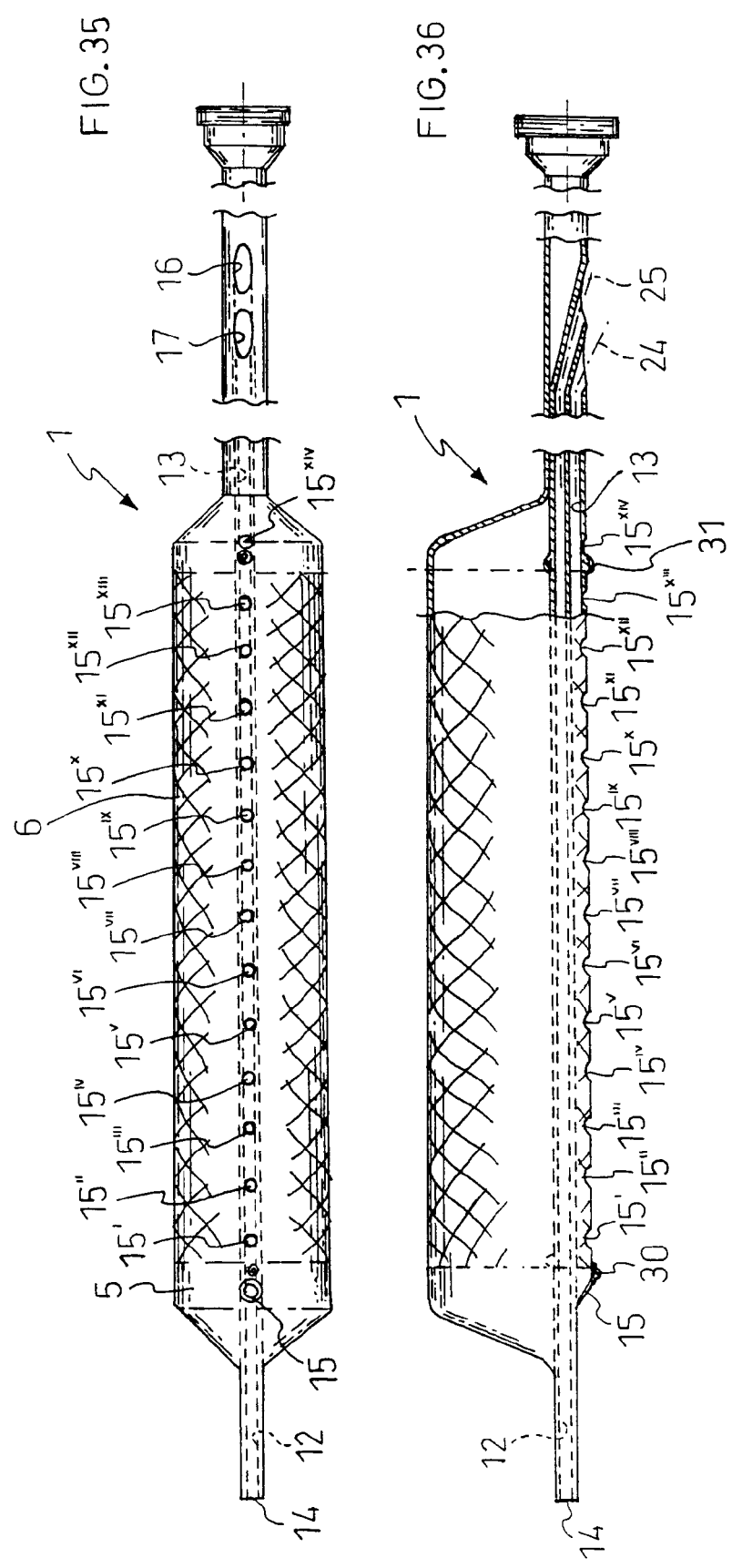

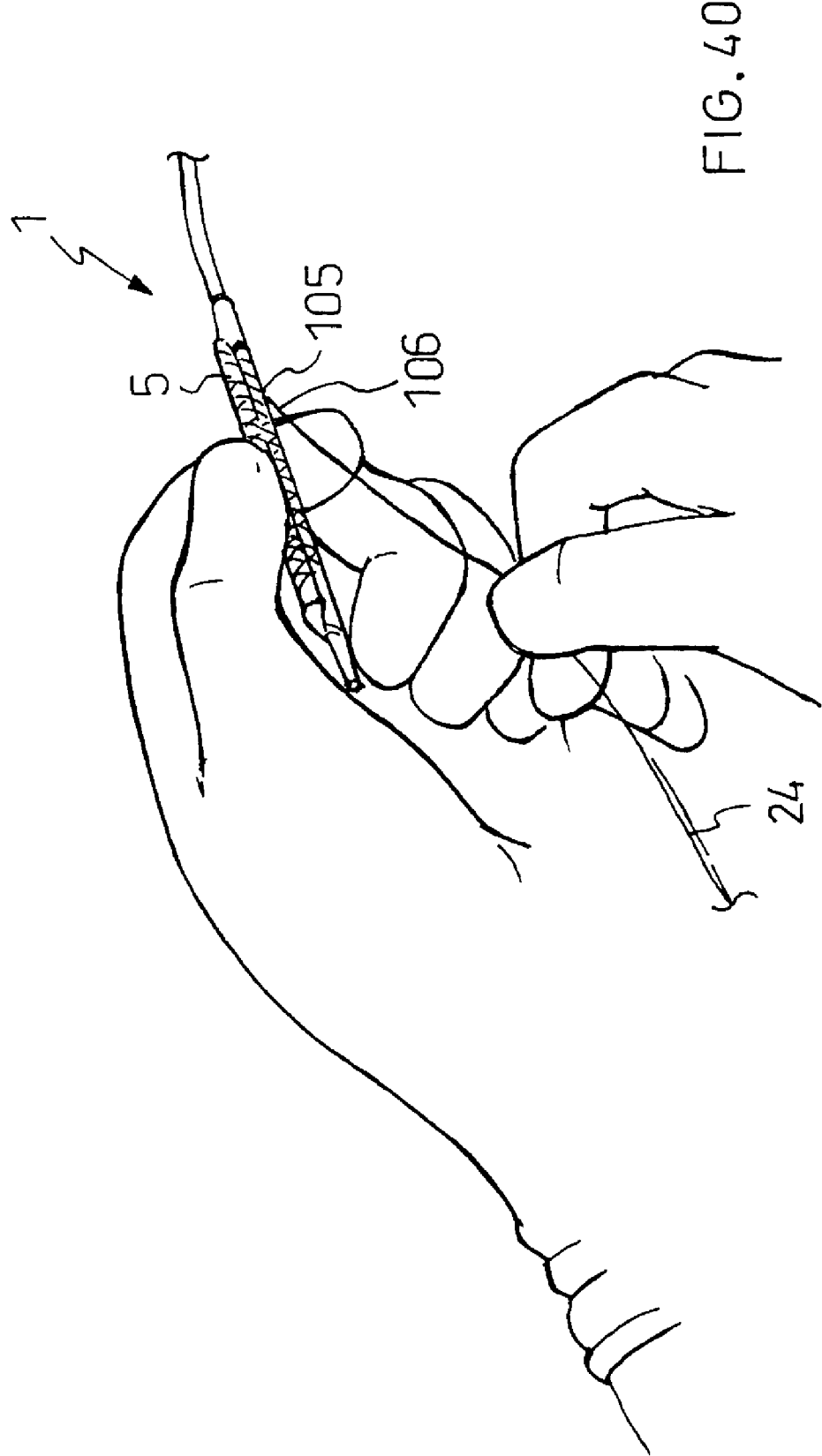

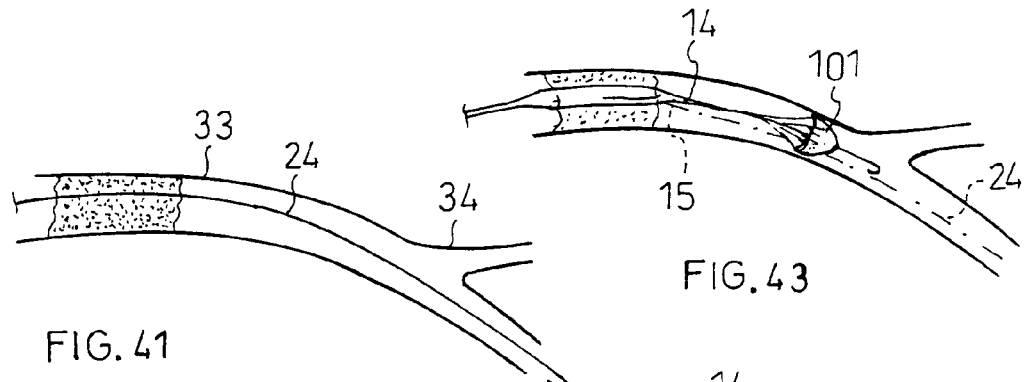
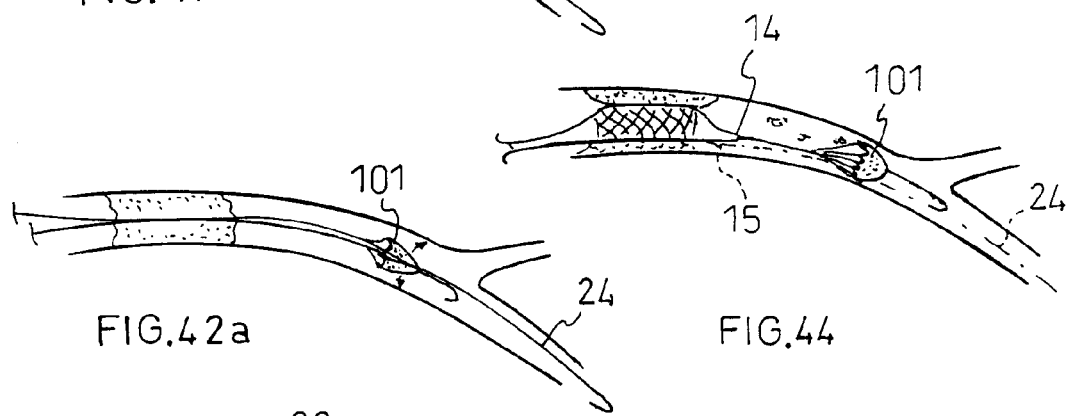
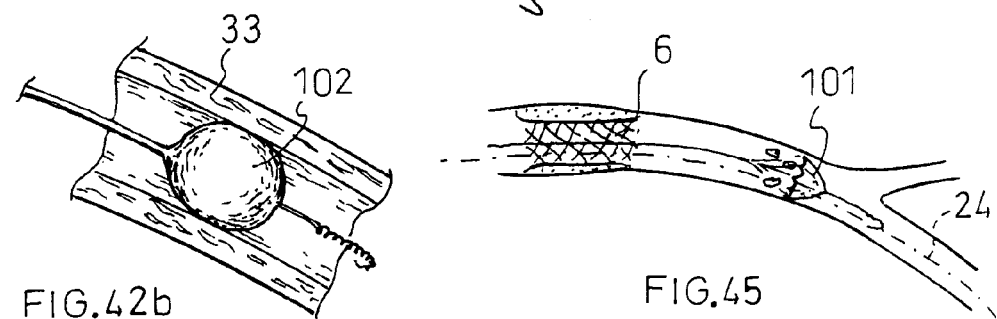
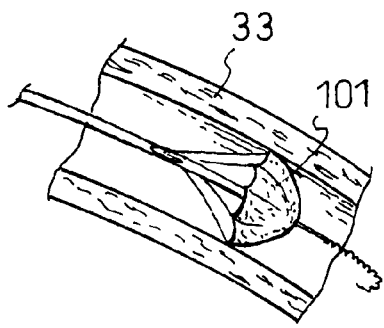

ENDOLUMENAL DEVICE FOR DELIVERING AND DEPLOYING AN ENDOLUMENTAL EXPANDABLE PROSTHESIS

This application is a divisional of U.S. patent application Ser. No. 10/204,251 filed on Nov. 26, 2002, now U.S. Pat. No. 7,540,879, which is a U.S. National Phase under 35 U.S.C. §371 of International Application No. PCT/EP00/12964, filed Dec. 19, 2000 and published in English on Jul. 8, 2004, which claims foreign priority from European Patent Application No. EP00200572.6 filed on Feb. 18, 2000, the full disclosure of all of which are incorporated by reference in their entirety herein.

The subject of the present invention is an endolumenal device for delivering and deploying an endolumenal expandable prosthesis. In particular, the present invention refers to a device for delivering and deploying an endolumenal expandable prosthesis at a bifurcation provided with a main conduit and at least a secondary conduit. Said device comprises an elongated body having a proximal end portion and a distal end portion. The distal end portion of said elongated body comprises expansion means having a longitudinally extended active portion removably engageable with the endolumenal expandable prosthesis and adapted to adjust said prosthesis from a radially collapsed condition to a radially expanded condition. The device further comprises a guidewire tracking means at least partially extending along said elongated body.

As is known, devices of the type described above are used for delivering and deploying, meaning in particular fitting or grafting, prostheses or stents endolumenally within conduit systems, such as for example vessels carrying body fluids and, in particular, lumens in the bodies of human beings and animals. Said vessels for the transportation of fluids are, for example, arterial blood vessels, such as coronary, peripheral and cerebral arteries, veins or gastrointestinal tracts.

Using the abovementioned devices it is possible, for example, to deploy endolumenal prostheses, or stents, in a vessel in which atherosclerotic stenoses, or plaque, has partially or completely occluded the lumen. Said prosthesis forms a radial support for the surrounding wall of the lumen and prevents it partially or completely occluding again, once it has been dilated by the expansion means (balloon). These procedures are carried out using known angioplasty techniques. Techniques of this type are, for example, described in the publication "The New Manual of Interventional Cardiology" edited by Mark Freed, Cindy Grines and Robert D. Safian, Division of Cardiology at William Beaumont Hospital, Royal Oak, Mich.; Physicians' Press 1996.

It is also known that the use of said techniques of angioplasty for percutaneous revascularization is increasingly used as an alternative to standard surgical procedures such as by-bass and thromboendoatherectomy.

Stent use, originally limited to cases of acute periprocedural complications following simple balloon angioplasty, such as dissection, thrombosis and acute occlusion, now applies also to elective treatment of coronary and systemic atherosclerotic lesions.

The widespread use of these techniques is considerably limited by the significant difficulties presented by the known endolumenal devices when they are used on vascular ramifications or bifurcations of the system of conduits (bifurcation lesions).

It is known that procedures on bifurcation lesions are frequently subject to failures and acute complications, because the known devices may cause occlusion of that branch of the bifurcation which operates near the segment of the lumen in which the prosthesis is fitted.

In particular, due to the activation of the expansion means in a first branch of the bifurcation, the atheromatous material of the plaques is protruded and displaced until it obstructs the ostium of a second branch of the bifurcation, (a problem known as "snow-plow" or "plaque-shifting").

Due to the abovementioned "snow-plow" or "plaque-shifting", the ostium and the lumen of the occluded branch must again be rendered accessible, or regained, by re-introducing a guidewire through a barrier consisting of the plaque previously protruded and displaced until it obstructed the lumen.

In other words, it is necessary, following the implanting of the first prosthesis, to insert a second guidewire and a second prosthesis into the occluded branch, passing through the mesh, or struts, of the first prosthesis. Even when it is possible to regain access to the occluded branch, the procedure becomes extremely lengthy and, in any case, the results depend very much on the experience of the surgeon.

Where the above described bifurcation lesions are present it is therefore essential that the procedure is carried out in highly qualified centres, fully equipped for cardiac surgery, that may be called upon urgently in the case periprocedural complications or lack of success in dilating the lesion or regaining the ostium of the side branch.

Due to the abovementioned difficulties, the use of stents with wide cells or apertures to allow the introduction of a guidewire into the side branch and the passage of a second stent has been proposed. However these wide cells can give rise to an increase in prolapse of plaque material through the meshes, or struts, and, therefore, to imperfect re-vascularization and increased probability of re-stenosis.

One alternative is the simultaneous use of two devices fitted with expansion means for the simultaneous insertion of two stents in each of the branches of the bifurcation (paired or kissing devices), or of a single bifurcated stent.

This known solution however is very bulky and difficult to manoeuvre and can only be used in large vessels and in proximal segments of the arterial tree. In other words, it is impossible to use this known solution in peripheral branches, where the presence of atherosclerotic plaques is more common. Furthermore, in order to insert the known paired devices it is necessary to use large-diameter guide-catheters. Said large diameter guide-catheters induce an higher periprocedural risk. In addition, the greater bulk of the paired devices occludes the vessel during insertion causing ischemia during the procedure and making it impossible to inject an adequate amount of contrast medium which is useful for visualizing the path for the correct positioning, first of the guidewire and then of the endolumenal devices fitted with the prosthesis.

The use of paired devices also lacks versatility, above all in the case of a single bifurcated stent, since the three vascular segments which make up the bifurcation—the proximal main vessel, the main vessel distal to the bifurcation and the secondary vessel, or side branch—may be of very different bores with lesions of varying lengths. It is therefore impossible at present to prepare a range of bifurcated stents which can be adapted to all the possible anatomical and pathological variables. It must also be noted that these bifurcated stents, of fixed dimensions, often occlude other branches near the bifurcation lesions, with consequent ischemia or incomplete revascularization.

It is therefore evident that not all bifurcation lesions, and in particular coronary bifurcation lesions, can be dealt with percutaneously.

The above considerations show that the need for an endolumenal device for delivering and deploying an endolumenal expandable prosthesis, which can reach both the branches of a bifurcation safely and rapidly, is widely felt.

Devices of this type are known from EP 0 897 700, WO 98 36709 and WO 99 15103.

A need is likewise felt to be able to fit endolumenal prostheses which are morphologically adaptable to the anatomy and to the pathology of the proximal and distal portions of the branches of the bifurcation. In other words, it is desirable to be able to deal with all types of lesions using a single endolumenal device, of the type described above, capable of adapting to a vast range of vessel diameters and lesions of any length. Said endolumenal device must also ensure the accurate deployment of the prosthesis, guaranteeing wide coverage of the bifurcation, which prevents protrusion of plaque material between the various prostheses fitted and the formation of re-stenosis.

Therefore, the object of this invention is to devise and make available an endolumenal device of the type specified above, which will meet all the abovementioned requirements and, at the same time, make it possible to avoid all the pitfalls outlined.

This object is achieved by means of an endolumenal device for delivering and deploying an endolumenal expandable prosthesis at a bifurcation provided with a main conduit and at least a secondary conduit, comprising an elongated body having a proximal end portion and a distal end portion; the distal end portion of said elongated body comprising expansion means having a longitudinally extended active portion removably engageable with the endolumenal expandable prosthesis and adapted to adjust said prosthesis from a radially collapsed condition to a radially expanded condition; a guidewire tracking means at least partially extending along said elongated body. Said device is characterised by the fact that said active portion of the expansion means is longitudinally associated to the elongated body in order to expand said prosthesis eccentrically from one side with respect to the elongated body, in order to leave free from said expanded active portion the other side of the elongated body, and in that—said guidewire tracking means comprises at least a guidewire lumen at least partially extending inside said elongated body, having at least a guidewire distal port provided on a side of the elongated body opposed to the expansion means and suitable for slipping through it a guidewire portion of at least a guidewire placeable with its distal portion in said main or at least a secondary conduit.

The subject of the present invention also includes a method for assembling out of an human body said endolumenal device to guidewires, said guidewires being positioned along a common proximal section of path and a diverging distal section of path, forming a bifurcation between said sections, employing the following stages:

said endolumenal device is fitted onto a proximal end of a first guidewire so that said first guidewire is received in a guidewire lumen through a first distal guidewire port;

said endolumenal device is fitted onto a proximal end of a second guidewire so that said second guidewire is received in the guidewire lumen through a second distal guidewire port;

said endolumenal device is advanced along said guidewires until at least part of the distal end portion of the elongated body is positioned beyond the bifurcation of the guidewires.

The subject of the present invention also includes a method for assembling out of an human body said endolumenal device to guidewires, said guidewires being positioned along a common proximal section and a diverging distal section of path, forming a bifurcation between said sections, employing the following stages:

said endolumenal device is fitted onto a proximal end of a first guidewire so that said first guidewire is received in a guidewire lumen through a first distal guidewire port;

said endolumenal device is fitted onto a proximal end of a second guidewire so that said second guidewire is received in the guidewire lumen through a second distal guidewire port;

said endolumenal device is advanced along said guidewires until at least part of the distal end portion of the elongated body is positioned on a distal diverging section of path of one of the guidewires.

Further characteristics and advantages of the endolumenal device according to the invention will become evident from the description that follows of some preferred embodiments, which are given purely by way of indication and without implying any limitation, with reference to the enclosed drawings, in which:

FIGS. 2 and 3 show a view from beneath, and a side view, of a detail of the device of FIG. 1;

FIGS. 4 and 4a show the enlarged cross section on IV-IV of the device of FIG. 2, according to two embodiments;

FIG. 5 shows an end view along the arrow V of the endolumenal device of FIG. 3;

FIGS. 6a and 6b show a partially sectioned view of the device of FIG. 1 during two stages of use;

FIGS. 7 and 8 show a view from beneath, and a side view, of a detail of an endolumenal device according to a second embodiment;

FIG. 9 shows the enlarged cross section on IX-IX of the device of FIG. 7;

FIG. 10 shows a front view along the arrow X of the device of FIG. 8;

FIGS. 11a and 11b show a partially sectioned perspective view of the device of FIG. 7 during two stages of use;

FIGS. 18 to 23 show a cross portion through a 'Y bifurcation' during six stages in the deploying of endolumenal prostheses;

FIGS. 24 and 25 show a view from beneath, and a side view, of an endolumenal device provided with two distal ports at the distal end of the body beyond the prosthesis;

FIG. 26 shows an enlarged section on XXVI-XXVI through the device of FIG. 24;

FIG. 27 shows a view along the arrow XXVII of the device of FIG. 25;

FIGS. 31 and 32 show a view from beneath, and a side view partially sectioned, of details of an endolumenal device having a plurality of guidewire lumens associated to a plurality of distal ports;

FIGS. 33 and 34 show a perspective view and a side view, in partial section, of an endolumenal device having a single guidewire lumen associated to an apical distal port and a plurality of distal ports spaced out along the body;

FIGS. 35 and 36 show a view from beneath, and a side view partially sectioned, of details of an endolumenal device having a first guidewire lumen associated to an apical distal port and a second guidewire lumen associated to a plurality of distal ports spaced out along the body;

FIG. 40 shows a perspective view, partially sectioned, during a stage in the slipping of a guidewire proximal end into the body fissure of the device of FIG. 38;

FIGS. 41 to 45 show a cross portion through a vessel during five stages in the deploying of an embolization containment device and of an endolumenal prosthesis;

FIG. 42c shows a detail in an enlarged scale of FIG. 42a;

FIG. 42b shows a cross portion through a vessel during a stages in the deploying of an embolization containment device according to a further embodiment;

Figure 1:
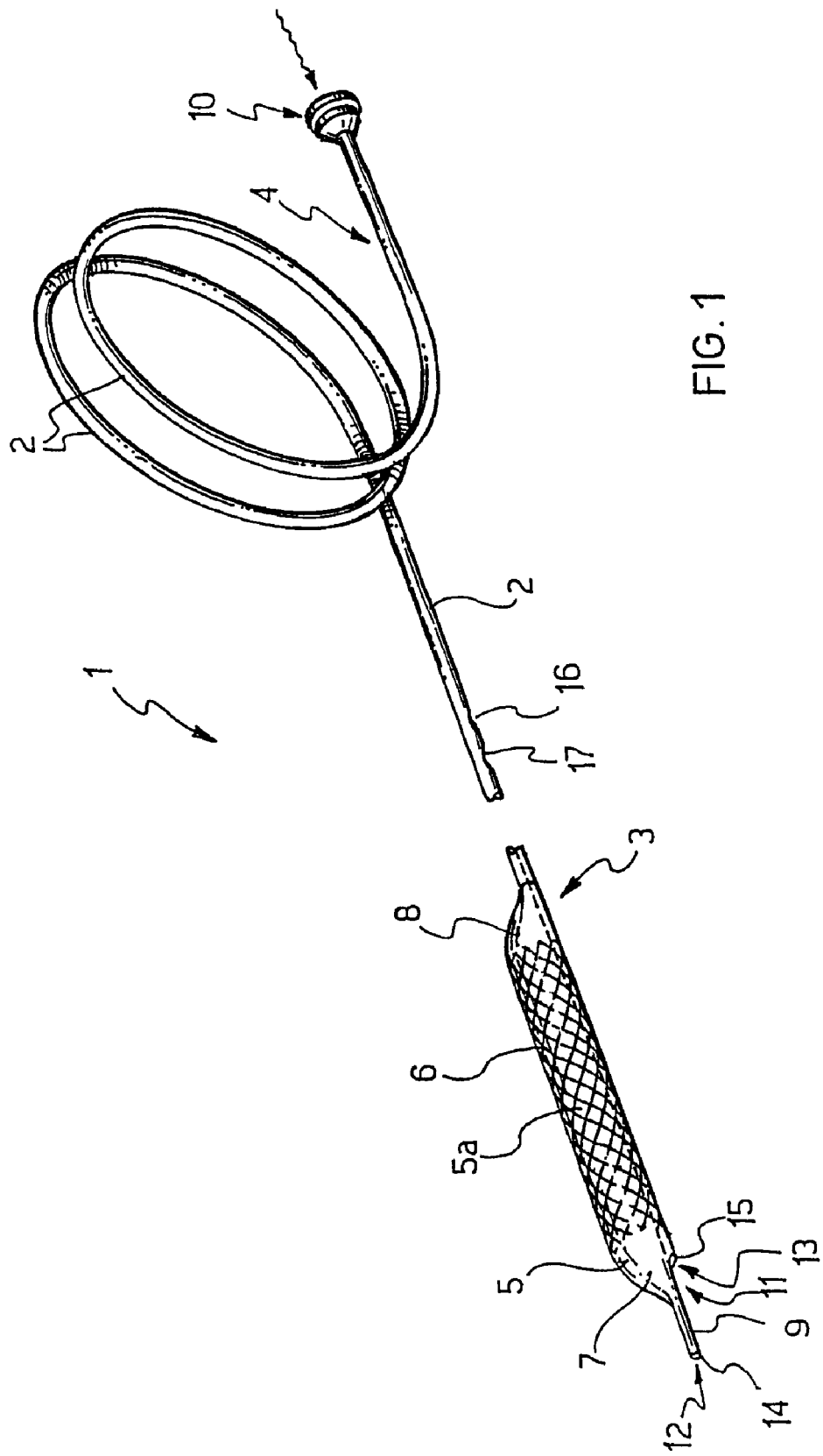
FIG. 1 shows a partially sectioned view of the endolumenal device fitted with a prosthesis.

With reference to the above figures, the number 1 indicates as a whole an endolumenal device for delivering and deploying an endolumenal expandable prosthesis, or balloon catheter. For example, said device is suitable for deploying an endolumenal expandable prosthesis at a bifurcation provided with a main conduit and at least a secondary conduit. The endolumenal device includes an elongated body 2 having a distal end portion 3 and a proximal end portion 4. For example, said elongated body 2 is between 100 cm and 160 cm in length, and preferably between 115 cm and 140 cm. The distal end portion 3 includes expansion means, 5, which can be removably engaged with an endolumenal expandable prosthesis 6. Said expansion means 5 can adapt said prosthesis 6 from a radially collapsed to a radially expanded position, in a manner which will be described in greater detail below. The expansion means 5 include a distal portion 7 of the expansion means a proximal portion 8 of the expansion means and a central portion 5a of the expansion means to which the prosthesis 6 can be attached. The distal portion of the elongated body 3 extends beyond the expansion means 5 in an apical portion 9. At the proximal end of the proximal end portion 4 of the elongated body 2, there are means 10 for connecting the endolumenal device 1 to an apparatus of a type known per se for the controlled activation of the expansion means 5. The endolumenal device 1 also includes guidewire tracking means 11 which extend at least partially along the elongated body 2. For example, said means 11 extend along the distal end portion 3 of the elongated body 2 close to the expansion means, 5 (FIG. 1).

Advantageously, the active portion of the expansion means is longitudinally associated to the elongated body in order to expand said prosthesis eccentrically from one side with respect to the elongated body, in order to leave free from said expanded active portion the other side of the elongated body.

With further advantage, the guidewire tracking means 11 comprises at least a guidewire lumen 12 or 13 that at least partially extends inside said elongated body 2. Said lumen has at least a guidewire distal port 15 provided on a side of the elongated body opposed to the expansion means and suitable for slipping through it a guidewire portion of at least a guidewire placeable with its distal portion in a main or at least a secondary conduit.

In one embodiment of the invention, a first guidewire lumen 12 and a second guidewire lumen 13 extend completely inside the elongated body 2. Distal ports 14, 15 and proximal ports 16, 17 make said first and second lumens 12, 13 able to receive guidewires 24, 25 (FIG. 19).

The distal ports 14, 15 are preferably spaced out along the elongated body 2. For example, the distal port 14 of the first guidewire lumen 12 is provided at the distal end of the apical portion 9, and the distal port 15 of the second guidewire lumen 13 is provided near the distal end of the expansion means 5 (FIGS. 1-3, 6a, 6b, 18-23). The proximal ports 16, 17 are preferably positioned in the portion of the elongated body 2 that lies between its proximal end and the expansion means 5. For example, said ports 16, 17 are located at a distance ranging between 90 cm and 130 cm, and preferably, between 105 cm and 115 cm, from the proximal end, or from the connector means 10 (FIG. 1).

According to one embodiment, said endolumenal device is a balloon catheter for angioplasty, 1. Said balloon catheter 1 comprises a tubular catheter 2, a proximal connector 10, and an inflatable balloon 5.

The catheter body 2 is tubular. The proximal portion 4 of said tubular body 2 is designed to support and push the distal portion 3. Therefore said proximal portion 4 is less flexible than the distal portion, which must be flexible in order to be able to enter the peripheral branches of a vessel. For example, said proximal portion 4 is made of a biocompatible material, such as biomedical steel or Nylon™. Moreover, said proximal portion 4 is designed to be received in a guide catheter (not shown and known per se) which is necessary for maintaining accessibility of the lumen of the vessel on which it is necessary to operate even when the endolumenal device 1 is withdrawn. Said guide catheter is also necessary for introducing, for example, a radio-opaque contrast medium into the vessel. The proximal portion 4 of the catheter body, 2 includes an inflation lumen, 18 (FIGS. 3, 4 and 4a, 6b). Said lumen 18 extends from the proximal end of the catheter body 2 to the inflatable balloon 5.

The proximal connector, 10, for example a connector commonly known as a "Luer", is provided at the proximal end of said portion 4 and forms the abovementioned means of connection of the endolumenal device 1 to the apparatus for the controlled activation of the balloon 5. For example, said connector connects the inflation lumen 18 of the balloon 5 to a pressurized fluid source.

The balloon 5 is associated with the distal portion 3 of the catheter body 2 to form an inflation chamber 19 which at least partially surrounds the catheter body (FIG. 3). The inflation chamber 19 is delimited by a balloon wall 20 equipped with an external envelope 22. Said inflation chamber 19 is in communication with the inflation lumen 18. In one embodiment, the balloon includes, between a distal portion 7 and a proximal portion 8, a central portion 5a. Said central portion 5a, when it is in a radially expanded, or inflated position, is roughly cylindrical. The balloon wall 20 in one embodiment is non-extendable or rigid when subjected to pressurized fluid. Therefore the balloon wall 20, when it is in a radially collapsed position, is folded around the catheter body 2, for example it is threefolded or, in other words, forms three folds 21 (FIG. 6a). By means of the external envelope 22, the balloon wall 20 can be removably fitted with an endolumenal prosthesis. For example, the external envelope is removably fitted with an endovascular stent, plastically deformable from a radially collapsed condition to a radially expanded condition, which can be fixed by pressure to the internal surface of a vessel wall. For example, said stent is a metallic tubular stent comprising struts or mesh. For this reason, the diameter of the central cylindrical portion 5*a*, when the balloon is radially expanded or inflated by pressurized fluid injected through the inflation lumen 18, is such as to fix said prosthesis to the wall of the vessel by pressure (FIG. 6*b*).

In a preferred embodiment of the invention, a longitudinal portion of the balloon wall 20 is associated internally with the catheter body 2. In other words, said wall 20 is fixed along its entire length to the catheter body, so that when the balloon 5 changes from the radially collapsed or deflated position to the radially expanded or inflated position, said balloon 5 will extend eccentrically or asymmetrically with respect to the catheter body 2, or in other words, on only one side of the body (FIGS. 3, 5 and 6*b*).

The distal portion 7 and the proximal portion 8 of the balloon 5 are advantageously tapered in shape. In particular, said portions are truncated cones.

Advantageously, the tubular catheter body 2 comprises sheath means or sleeve means 23, for example a flexible conduit. For example, said sheath means are an integral part of the elongated body. The sheath means 23 include a tubular body through which run a number of longitudinal lumens, 12, 13 forming the above-mentioned guidewire lumens. The guidewire lumens 13, 14, or sections of these, advantageously run in parallel along the elongated body. Said lumens debouch at the extremities of the sheath means with the above-mentioned guidewire ports 14, 15, 16, 17. Said sheath means 23 are located inside the tubular catheter body 2 in such a way as to leave a space (which forms the above-mentioned inflation lumen 18) along the entire length of that portion of the catheter body 2 which is situated between the proximal connector 10 and the balloon 5. Preferably, said sheath means are attached for their entire length to the portion of the wall delimiting the balloon inflation chamber (FIGS. 3, 4, 4*a* and 6*b*). In other words, where the tubular elongated body of the catheter continues in the balloon wall, said sheath means are associated to a portion of the balloon wall. In one embodiment, said sheath means extend beside the balloon distal portion becoming said catheter body apical portion. The extremities of the sheath means 23 are attached to the wall of the catheter body in such a way as to make the guidewire lumens accessible from outside the catheter body through the guidewire ports.

It is particularly advantageous when said sheath means 23 debouch in a first distal guidewire port 14, of a first guidewire lumen 12, distant from a second distal guidewire port 15 of a second guidewire lumen 13.

In particular, said sheath means extend to the tip of the distal portion 3 of the catheter body 2 in such a way as to debouch with the first distal guidewire port to the tip of the apical tract 9.

In a first embodiment of the invention, thanks to the asymmetrical position of the balloon 5 with respect to the catheter body 2, the second distal guidewire port 15 is positioned along the catheter body 2 so as to allow the second guidewire lumen 13 to debouch at the distal end of the central portion 5*a* of the balloon, or in other words, so as to be positioned just outside the prosthesis 6 attachable to the balloon 5 (FIGS. 1 to 6*b*).

In a second embodiment of the invention, the second distal guidewire port 15 is positioned along the catheter body in such a way that the second guidewire lumen 13 debouches at a point located between the distal portion 7 and the proximal portion 8 of the balloon 5, and in particular at a point of the central portion 5*a* attachable to the prosthesis 6. For example, said port 15 is located near the centre line of said central portion 5*a* (FIGS. 7, 8, 11*a* and 11*b*). Preferably, the prosthesis 6, which can be attached to said catheter 1, has a window 26 designed to prevent obstruction of said distal guidewire port 15 when it is fitted on the balloon 5. For example, the prosthesis 6 has a wider cell 26 than the other cells of the prosthesis, and at the same time of a size close to that of the ostium of the lumen of the branch on which it is necessary to proceed, or only slightly smaller. Alternatively, the balloon can be fitted with a number of prostheses, placed side by side in order to avoid obstructing said port 15.

Preferably, the proximal guidewire ports 16, 17 are located in a portion of the catheter body 2 which, during use of the catheter 1, remains sheathed in the guide-catheter. For example, said proximal guidewire ports are located at a distance from the tip of the catheter ranging between 15 cm and 35 cm and, preferably between 20 cm and 30 cm. Alternatively, said ports 16, 17 are located at the proximal end of the catheter body. In this case the balloon catheter 1 is fitted with a proximal connector 10 with at least two channels. A channel for the admission of the pressurized fluid into the inflation lumen 18, and channels for passing the guidewires 24, 25 along.

Advantageously, radio-opaque markers, 30 and 31 are associated with the catheter body 2 (FIG. 3). For example, said markers are located along the catheter body 2 at the distal and proximal ends of the prosthesis 6.

Said catheter body also includes radio-opaque markers for the identification of the position along said body of the distal 14, 15, and/or proximal 16, 17 guidewire ports of the guidewire lumens 13, 14.

The subject of the present invention also comprises a kit for delivering and deploying an endolumenal expandable prosthesis. Said kit comprises an endolumenal device, 1, as described above, at least a couple of guidewires 24, 25, and at least one expandable prosthesis 6 radially associated with the expansion means 5 of said endolumenal device 1. Said prosthesis comprises a tubular prosthesis body adaptable from a radially collapsed condition, of minimal external diameter, to a radially expanded condition, of extended external diameter greater than the collapsed external diameter.

For example, said kit for delivering and deploying an endolumenal expandable prosthesis comprises at least one first radially expandable prosthesis associated with the proximal portion of the expansion means of said endolumenal device and also comprises at least one second radially expandable prosthesis associated with the distal portion of the expansion means of said endolumenal device, or alternatively a single prosthesis overlapping said proximal and distal portions of the expansion means.

Each of the guidewires of said kit includes means of identification, such as for example the colour of at least a proximal portion of the guidewire, or a diameter of the cross section of a proximal portion of the guidewire which differs for each guidewire.

Said guidewires advantageously comprise an elastically flexible distal end portion.

In particular, said guidewires include initial proximal sections which are positionable along a proximal section of path common to all the guidewires, and secondary distal sections which are positionable along distal sections of path which diverge and form with said proximal section of path a bifurcation. It is particularly advantageous for at least one of said guidewires to include an elastically flexible distal portion, which extends at least to straddle said bifurcation.

It is furthermore advantageous for said guidewires to include radio-opaque markers, for example located near the tip of the distal portion.

A description of the working of an endolumenal device according to this invention follows.

In particular, the procedures necessary for guiding an endolumenal device along guidewires 24, 25 are described below. Said guidewires are located along a common proximal section of path and a diverging distal section of path, forming a bifurcation between said sections. The above method comprises the following stages:

said endolumenal device is fitted onto a proximal end of a first guidewire so that said first guidewire is received in a first guidewire lumen through its distal guidewire port;

said endolumenal device is fitted onto a proximal end of a second guidewire so that said second guidewire is received in a second guidewire lumen through its distal guidewire port;

said endolumenal device is advanced along said guidewires until at least part of the distal end portion of the elongated body is positioned beyond the bifurcation of the guidewires.

Advantageously, it is possible to envisage a further method of guiding an endolumenal device along guidewires 24, 25, in which said guidewires are positioned along a common proximal section of path and a diverging, distal section of path, forming between said sections a bifurcation. This further method includes the following stages:

said endolumenal device is fitted onto a proximal end of a first guidewire so that said first guidewire is received in a first guidewire lumen through its distal guidewire port;

said endolumenal device is fitted onto a proximal end of a second guidewire so that said second guidewire is received in a second guidewire lumen through its distal guidewire port;

said endolumenal device is advanced along said guidewires until at least part of the distal end portion of the elongated body lies on a distal divergent section of path of one of the guidewires.

The steps of a method for fitting radially expandable prostheses to the walls of branches forming a 'T bifurcation' 32 are described below (FIGS. 12 to 17e). Said bifurcation 32 comprises a main conduit 33 and a collateral conduit 34 that branches off from a wall of the main conduit 33. The above-mentioned method comprises the following steps:

A kit as described above, and in particular a kit which comprises an endolumenal device having a distal guidewire port located on a central portion of the expansion means, is prepared.

Figure 12:
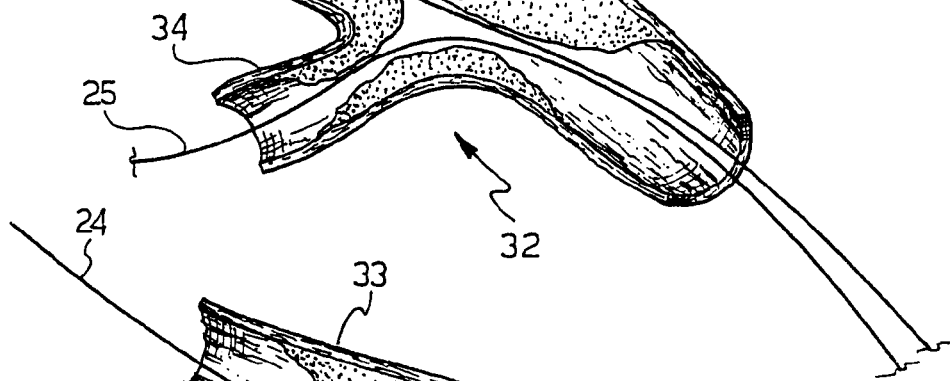
FIGS. 12 to 17c show a section through a 'T bifurcation' during eight stages in the deploying of endolumenal prostheses.

Then, through a proximal section of the main conduit, a first guidewire is positioned in the main conduit so that it passes the bifurcation, and a second guidewire is positioned in the collateral conduit. Said guidewires are positioned in such a way as to follow an initial proximal section of path together and second distal sections of path that diverge at said bifurcation (FIG. 12).

Next, a first endolumenal device, equipped with a radially expandable prosthesis, is fitted onto a proximal end of the second guidewire, so that said second guidewire is received in a guidewire lumen of the endolumenal device, through a distal guidewire port located on the tip of its elongated body.

Figure 13:
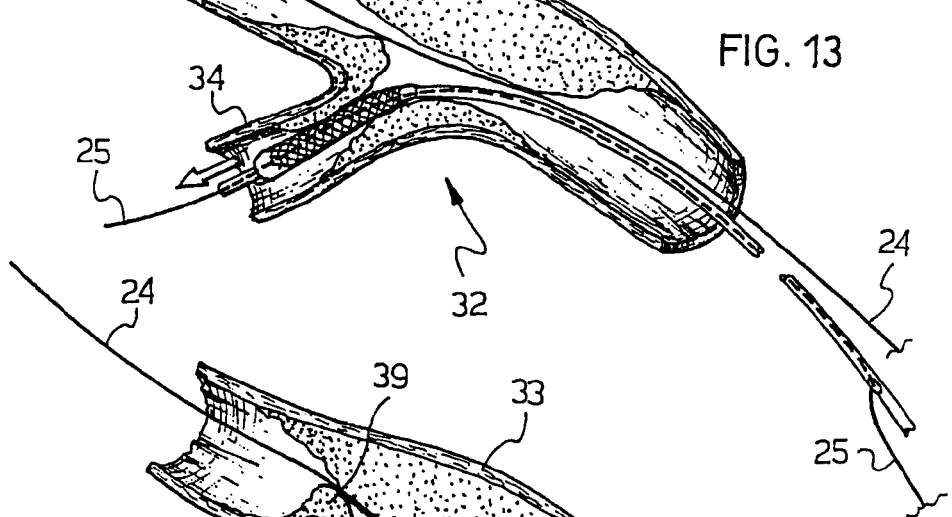

Said first endolumenal device is inserted into said conduits following the proximal and then the distal sections of path of the second guidewire in order to position the radially expandable prosthesis in the collateral conduit so that its proximal edge is positioned near an ostium of said collateral conduit (FIG. 13).

Figure 14:
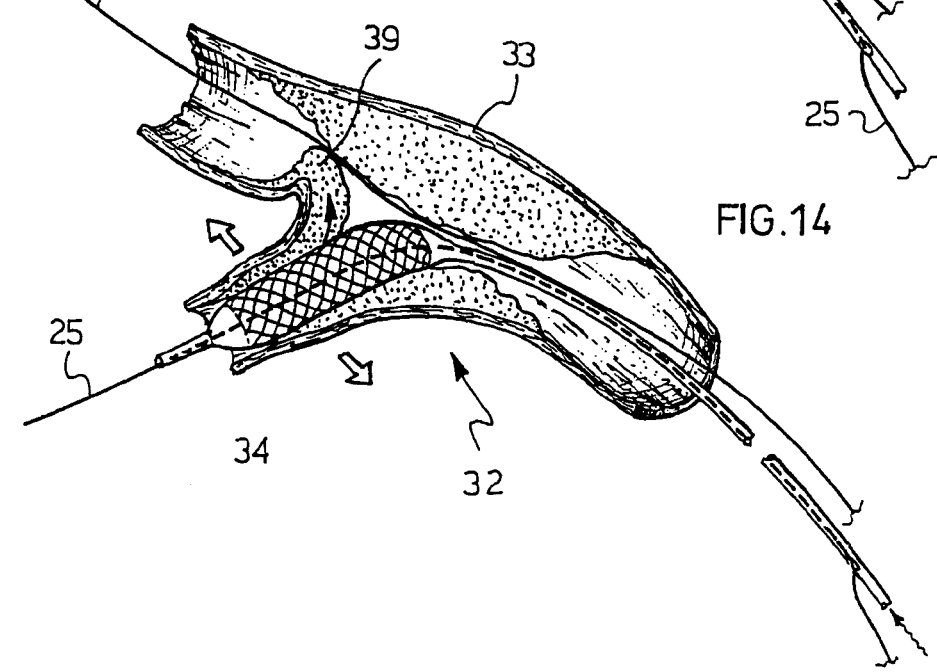
Figure 15:
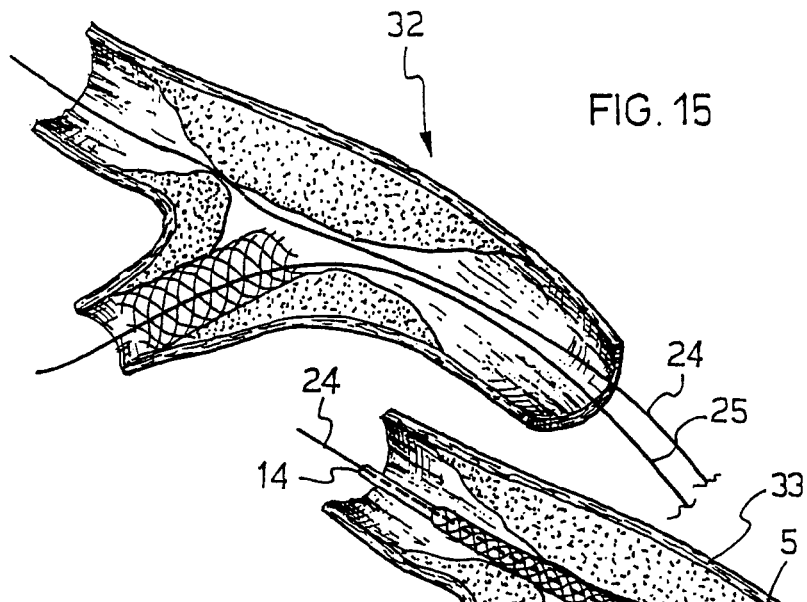

Said expandable means are then activated so that said prosthesis is in its radially expanded condition and fixed by pressure to the wall of the collateral conduit (FIG. 14).

Next, said expansion means are withdrawn and the first endolumenal device is withdrawn from the second guidewire until it has been removed from the conduits.

A second endolumenal device equipped with a radially expandable prosthesis is fitted onto a proximal end of the first guidewire so that said first guidewire is received in a first guidewire lumen through its distal guidewire port located on the tip of the endolumenal device. Said second endolumenal device is fitted onto a proximal end of the second guidewire so that said second guidewire is received in a second guidewire lumen through its distal guidewire port located on the portion of elongated body that lies between a distal and a proximal end of the expansion means.

Figure 16:
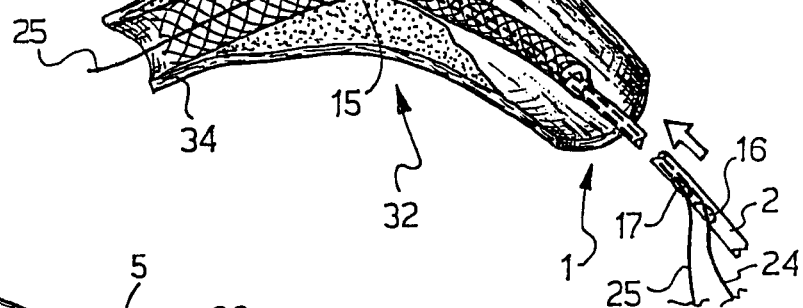

Said endolumenal device is inserted into the main conduit and slid along the proximal section of path of the guidewires until a distal portion of the endolumenal device, located between the tip of said device and the distal guidewire port of the second guidewire lumen, is positioned beyond the bifurcation (FIG. 16).

Figure 17A:
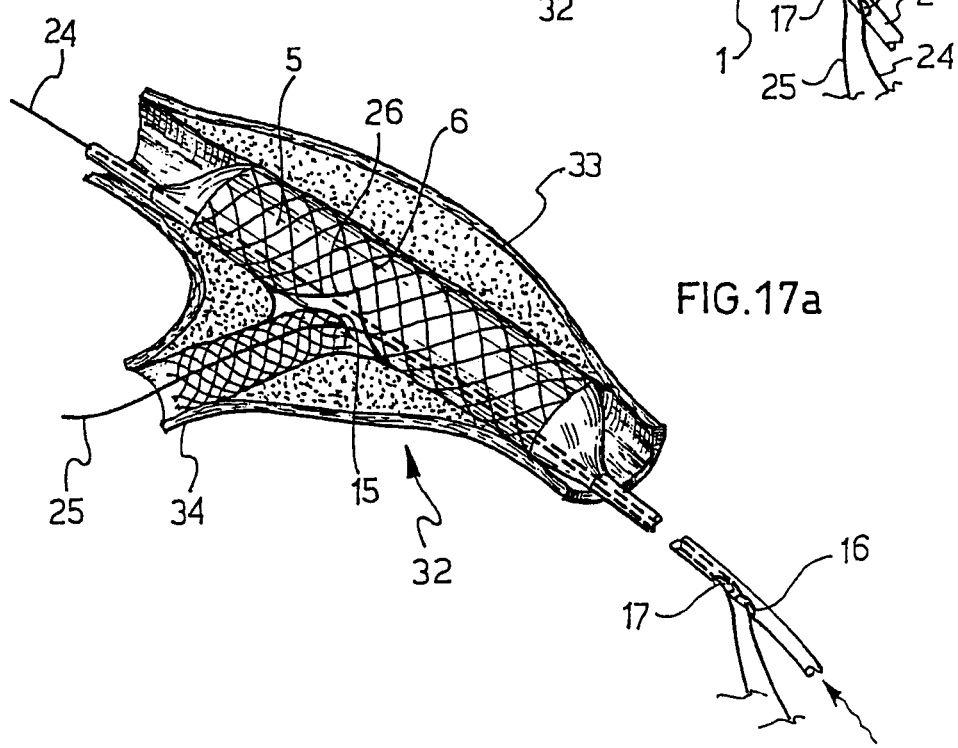
FIGS. 17d and 17e show in section two alternative stages in the deploying of prostheses in the bifurcation shown in FIG. 17c.
Figure 17B:
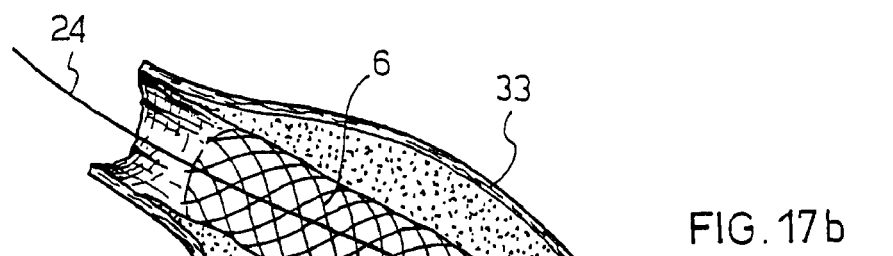

The expandable means of said second device are activated so as to bring said prosthesis into its radially expanded condition and fixed by pressure to the wall of the main conduit and straddling the bifurcation (FIG. 17a).

Finally said expansion means are withdrawn and then the second endolumenal device is withdrawn from the guidewires until it has been removed from the conduits.

Further steps which make it possible to adapt the previously grafted prostheses in order to cover the lesion completely are described below.

A third endolumenal device without a prosthesis is fitted onto the second guidewire, positioning it to straddle the bifurcation so that a distal portion of the expansion means enters the collateral conduit and a proximal portion of the expansion means is positioned in the main conduit.

Figure 17C:
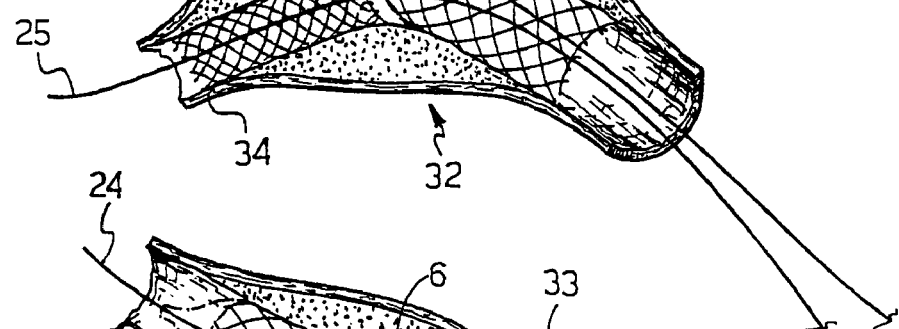
Figure 17D:
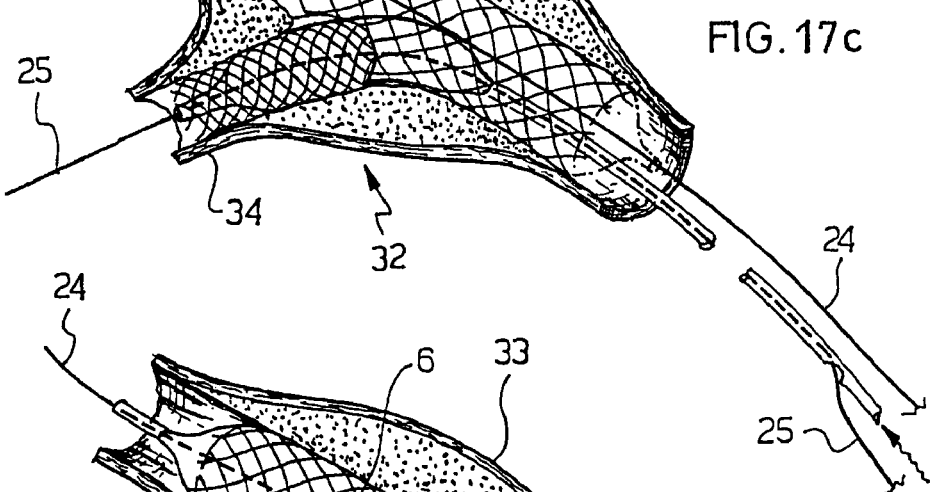
Figure 17E:
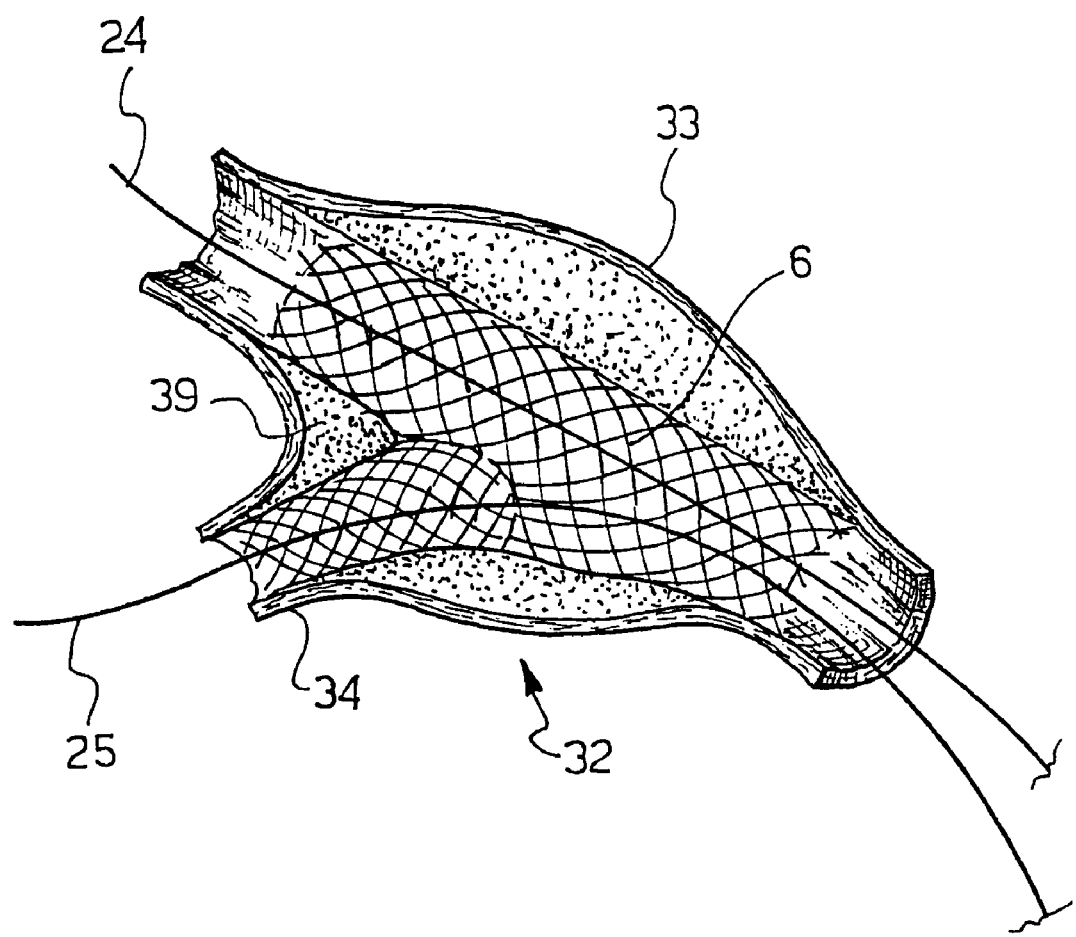

The expansion means of the third device are then activated so as to adapt a portion of the prosthesis in the main conduit facing the ostium or lateral window of the collateral conduit to the shape of the lumen of said collateral conduit (FIG. 17c).

Said expansion means are withdrawn and then the third endolumenal device is withdrawn from the second guidewire until it has been removed from the conduits.

By inflating the third endolumenal device (for example a balloon catheter for angioplasty) straddling the bifurcation, the struts of the prosthesis grafted in the main conduit is moulded so that it surrounds the ostium of the collateral conduit perfectly, and guarantees perfect coverage of the lesion area (FIG. 17c). Alternatively, particularly in the case of larger diameter or larger bore conduits it is possible to insert two balloon catheters simultaneously, fitting them on the guidewires 24, 25, so that they are paired and straddle the bifurcation, one in the main conduit and the second partially in the collateral conduit and partially in the main conduit. Simultaneous expansion of the two balloons shapes the prostheses so that they match and form a continuous support structure which covers the entire extension of the lesion and creates, in the area of the bifurcation, a funnel-shaped area which joins the main and the collateral branches and promotes non-vortical fluid flow in the conduits or vessels.

The stages of the method described above may also be reversed, grafting first the main vessel and then the collateral vessel.

In view of the above procedures it is evident that the grafting of a prosthesis in the main vessel shifts the plaque 39 material to obstruct the ostium of the collateral vessel or vice versa (FIG. 14). Thanks to the fact that, using the device according to the invention, the application of a first prosthesis in a vessel is always carried out leaving a second guidewire in a second branch, in spite of the presence in the ostium of the same of a barrier of plaque caused by "snow-plow" or "plaque-shifting". It is therefore always possible to insert in the second branch a device for the application of a second prosthesis. Using known prior-art devices it is not possible to operate simultaneously with two guidewires always present in the two branches of the bifurcation, because a second guidewire not positioned inside the prior-art device would be externally jailed by the prosthesis and rendered unusable. In other words, with the prior-art device it is necessary to proceed using only one guidewire per procedural stage. With the device according to the invention, however, it is possible to effect the swift exchange of the endolumenal device on guidewires which always remain in situ, it being possible to withdraw the endolumenal device from a first branch of the bifurcation to reinsert the same device or a second device in a second branch with extreme rapidity.

The steps for a further method for fitting radially expandable prostheses to the walls of the branches of conduits forming a 'Y bifurcation' 35 are described below. Said bifurcation comprises a proximal main conduit 36 and a first and a second secondary distal conduits 37, 38 which branch off from a distal end of the main conduit, forming between them a carina. Said method comprises the following steps.

A kit as described above is prepared, and in particular a kit comprising an endolumenal device fitted with a distal guidewire port located near the distal edge of a prosthesis fitted on the expansion means, and a second distal guidewire port located at the tip of the device, or apical port.

Through the main conduit first guidewire is positioned in the first secondary distal conduit and a second guidewire in the second secondary distal conduit, said guidewires being positioned so as to follow a first proximal section of path together and second distal section of path that diverge after said bifurcation (FIG. 18).

A first endolumenal device equipped with a radially expandable prosthesis is fitted onto a proximal end of the first guidewire, so that said first guidewire is received in a guidewire lumen of the endolumenal device through its distal guidewire port located at the tip of its elongated body.

Said first endolumenal device is fitted onto a proximal end of the second guidewire so that said second guidewire is received in a second guidewire lumen through its distal guidewire port located near the prosthesis distal edge, just beyond the prosthesis.

Said first endolumenal device is inserted into said conduits following the proximal section of path until the carina is positioned against the elongated body and near the distal guidewire port positioned near the distal end of the expansion means (FIG. 19).

Said expandable means are activated so as to bring said prosthesis into its radially expanded condition, fixed by pressure to the wall of the main conduit (FIG. 20).

Said expansion means are withdrawn and the first endolumenal device is then withdrawn from the guidewires.

A second endolumenal device equipped with a radially expandable prosthesis is fitted onto a proximal end of the first guidewire so that said guidewire is received in a guidewire lumen through its distal guidewire port located on the tip of said second endolumenal device.

A third endolumenal device equipped with a radially expandable prosthesis is fitted, at the same time as the second endolumenal device, onto a proximal end of the second guidewire so that said second guidewire is received in a guidewire lumen through its distal guidewire port located on the tip of said third endolumenal device.

Figure 21:
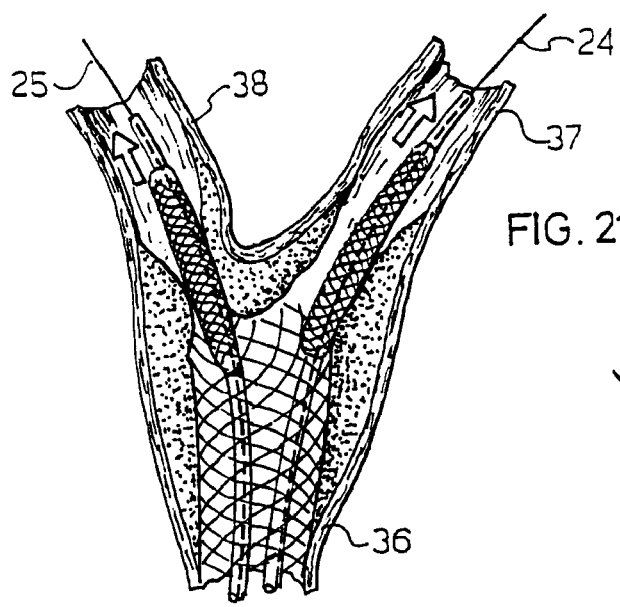

Said second and third endolumenal devices are simultaneously inserted into the main conduit and slid along the proximal section of path of the guidewires and then along the respective distal sections of path of said guidewires, until the expansion means are positioned in a proximal portion of said first and second secondary distal conduits, so that a proximal portion of the expansion means is positioned near the carina. In particular, care is taken to ensure that the proximal edge of both the second and third prostheses is in contact with the distal edge of the first prosthesis, already positioned and expanded in the main lumen (FIG. 21).

Figure 22:
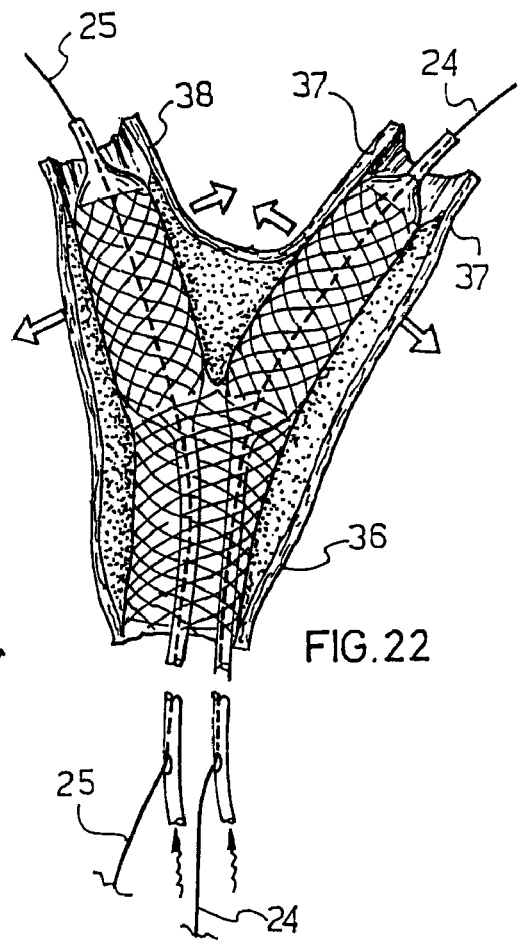

The expansion means of said second and third endolumenal devices are activated in order to bring the respective prostheses into a radially expanded condition fixed by pressure to the walls of said first and second distal conduits (FIG. 22).

Figure 23:
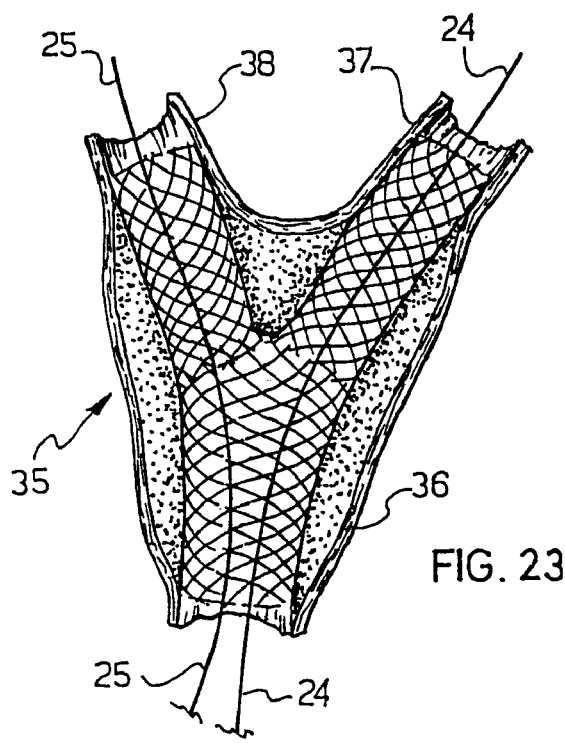
Figure 28:
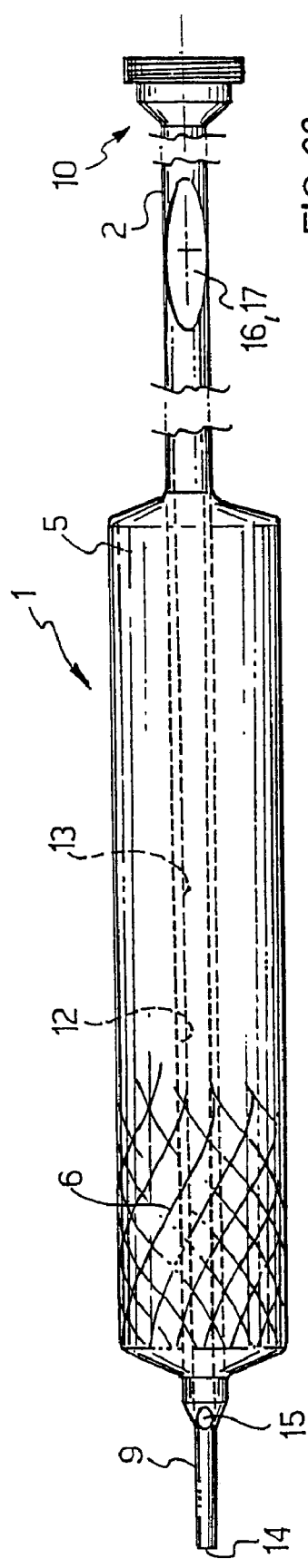
FIGS. 28 and 29 show a view from beneath, and a side view partially sectioned, of details of an endolumenal device having a single guidewire lumen associated to distal ports at the distal end of the body beyond the prosthesis.
Figure 29:
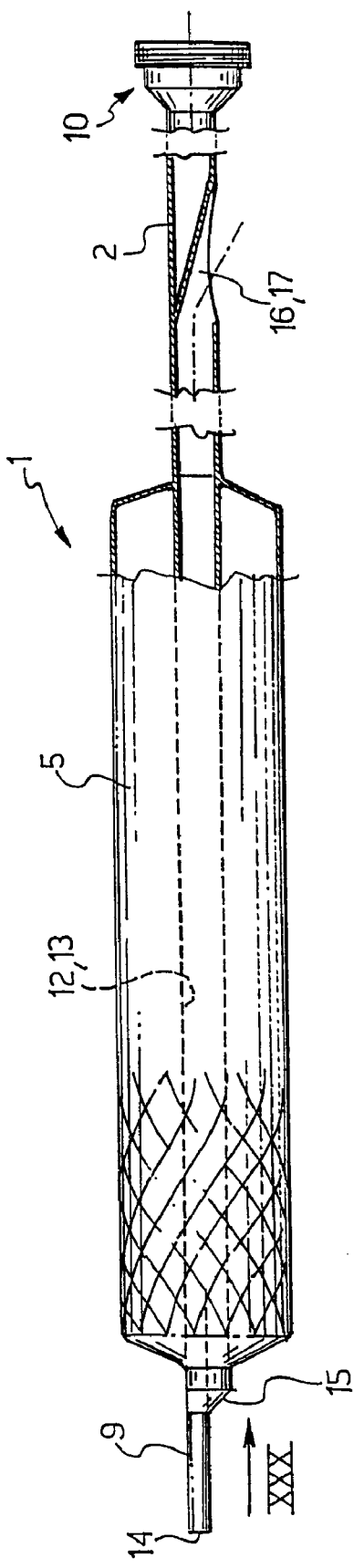
Figure 30:
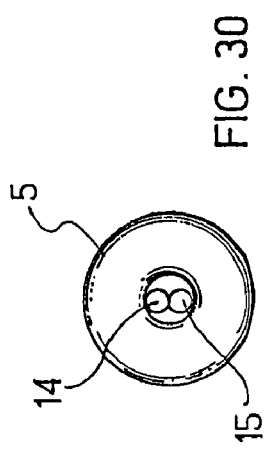
FIG. 30 shows a view along the arrow XXX of the device of FIG. 29.

Said expansion means are withdrawn and then the second and third endolumenal devices are withdrawn from the guidewires until they have been removed from the conduits (FIG. 23).

The above description shows how the use of at least two guidewire lumens which extend at least partially along the inside of the elongated body makes it possible to fit the endolumenal device simultaneously on at least two guidewires. In this manner, once at least two guidewires have been inserted in the branches of a bifurcation, it will be possible to insert and withdraw the endolumenal device from a first branch of the bifurcation without ever loosing rapid access to all the branches already negotiated, i.e. reached by guidewires. In other words, it will be possible to maintain uninterrupted access or vascular approach to all the branches of the vascular system on which it is necessary to operate and in which a guidewire has been inserted or, in yet other words, using the device proposed it is no longer necessary to break through the barrier of plaque 39 material which obstructs the ostium of the branch by "snow-plow" or "plaque-shifting".

Thanks to the endolumenal device according to the invention it will also be possible to position accurately a first endovascular prosthesis in the main vessel always with precise positioning and complete distension or application of the prosthesis over the entire area of the lesion, thus reducing the probability of re-stenosis and avoiding the pitfalls of the known techniques.

Advantageously, the endolumenal device proposed allows extreme flexibility and modularity in the application of the endolumenal prostheses. Thus, if the expansion means are positioned exactly straddling the bifurcation it is possible to deploy endolumenal prostheses of exactly the correct length and diameter for the dimensions of the segment of damaged vessel to be treated, by means of the proximal and distal portions of the expansion means.

With further advantage, each portion of the expansion means makes it possible to graft a number of endolumenal prostheses of optimal diameter and length for the anatomy of the damaged vascular branch.

When expansion means fitted to the endolumenal prostheses are in the collapsed position, the device according to the invention is of reduced transverse bulk, making it possible to reach peripheral branches extremely easily and rapidly (trackability).

Together with the versatility of application of prostheses adapted to different branches of the bifurcation, the device proposed also makes it possible to join prostheses, or, in other words, it allows total coverage of the damaged area, avoiding prolapse of atheromatous material and reducing the probability of re-stenosis.

A further advantage derives from the fact that, using the endolumenal device according to the invention, the geometry of the prosthesis is not distorted and the vascular anatomy is respected. In contrast, distortion of the prosthesis is inevitable when endolumenal devices according to the prior art are used.

Obviously, variations and/or additions to what is described above and illustrated may be envisaged.

Alternatively to a balloon with rigid walls threefolded onto the catheter body for insertion into the lumen of a vessel, as described above, it is possible to envisage the use of a compliant or extensible balloon.

Other possible variations are:
- the catheter of the type described above, "single-operator rapid exchange" or "monorail", may alternatively be of the "over-the-wire" type, that is with opening of the proximal guidewire lumens at the proximal end of the elongated body;
- one of the at least two guidewire lumens may always be occupied by a guidewire and may be inserted in the conduit, or vessel, together with the endolumenal device. Preferably, in this case the guidewire is fastened to or an integral part of the elongated body of the endolumenal device, for example extending from the apical portion of this ("fixed-wire").
- the catheter may also be of the perfusion balloon type in which passages are provided for fluid flow when the balloon is inflated: these provide communication between the portions of elongated body above and below the expansion means (passages for the blood in the body to prevent temporary occlusion of the vessel during the application of the prosthesis and the inflation of the balloon).
- The endovascular prosthesis may be modular. For example it is possible to provide a series of prostheses of set diameters and a series of set lengths which the operator can crimp to the proximal and distal portions of the expansion means, making them extremely flexible or, in other words, making it possible to adapt the prosthesis perfectly to the pathological requirements of the moment, or in other words, to the size of the lesion and the bore of the lumen of the vessel on which it is necessary to operate.

As an alternative to the above description, illustrated by FIGS. 3 and 8, at least one portion of said at least a couple of guidewire lumens 12, 13 forms a single guidewire lumen (FIGS. 28, 29, 30, 33 and 34).

In a further variation of the invention, a guidewire lumen 13 have distal ports 15 located near the proximal end of the expansion means, 5. Instead of the embodiment illustrated, for example, in FIG. 2 or 3, the elongated body is attached externally to the wall of the balloon.

In a further embodiment of the invention, said expansion means are designed to hold a self-expanding prosthesis in a radially folded position and release it in a controlled manner so that it takes up a radially expanded position. Said expansion means include a sheath designed to receive in a sheath lumen said self-expanding prosthesis. Said sheath can advantageously be adapted in controlled manner from a first constricted position in which the self-expanding prosthesis is confined in said lumen of the sheath, to a second released position, in which said prosthesis is released from said lumen of the sheath so that said prosthesis is radially free, to bring itself into the radially expanded condition.

Such a device can be advantageously used in the artificial conduits of biomedical equipment that connects up to the patient's body. For example, a device of the type described above can be used for transporting, positioning and deploying an element for the repair of the walls of a conduit accidentally damaged during the use of the abovementioned machinery.

Advantageously, the endolumenal device 1 comprises at least a guidewire lumen 12 or 13 extended completely inside the elongated body 2.

With further advantage, the active portion of the expansion means is entirely associated to the elongated body in order to expand said prosthesis exclusively from one side with respect to the elongated body, and in order to leave free from said expanded active portion the other side of the elongated body.

Figure 37:
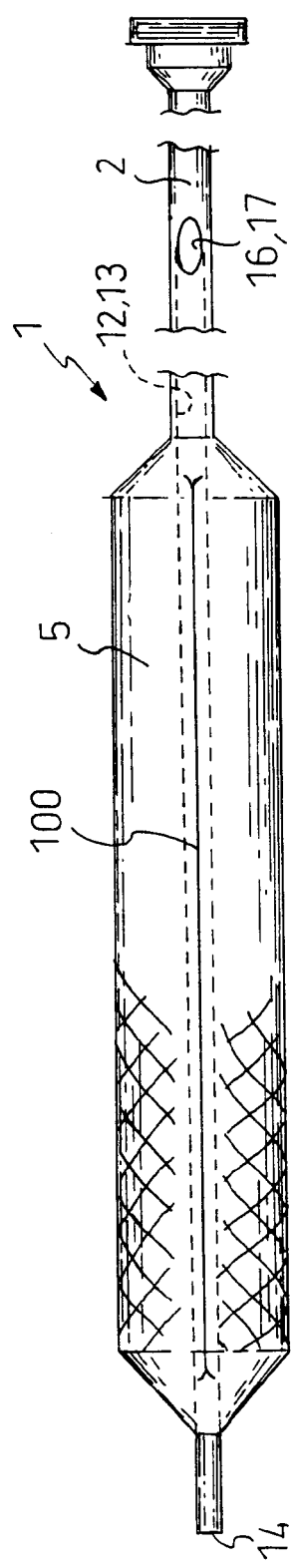
FIGS. 37, 38 and 39 show a view from beneath, and a side view partially sectioned, and an enlarged sectioned prospective of details of an endolumenal device having a fissure suitable for realising a distal port.
Figure 38:
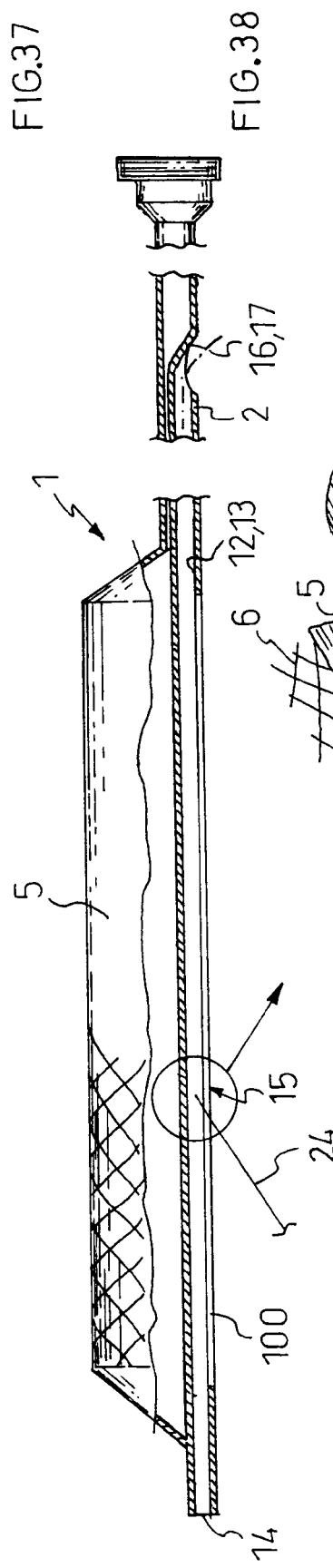
Figure 39:
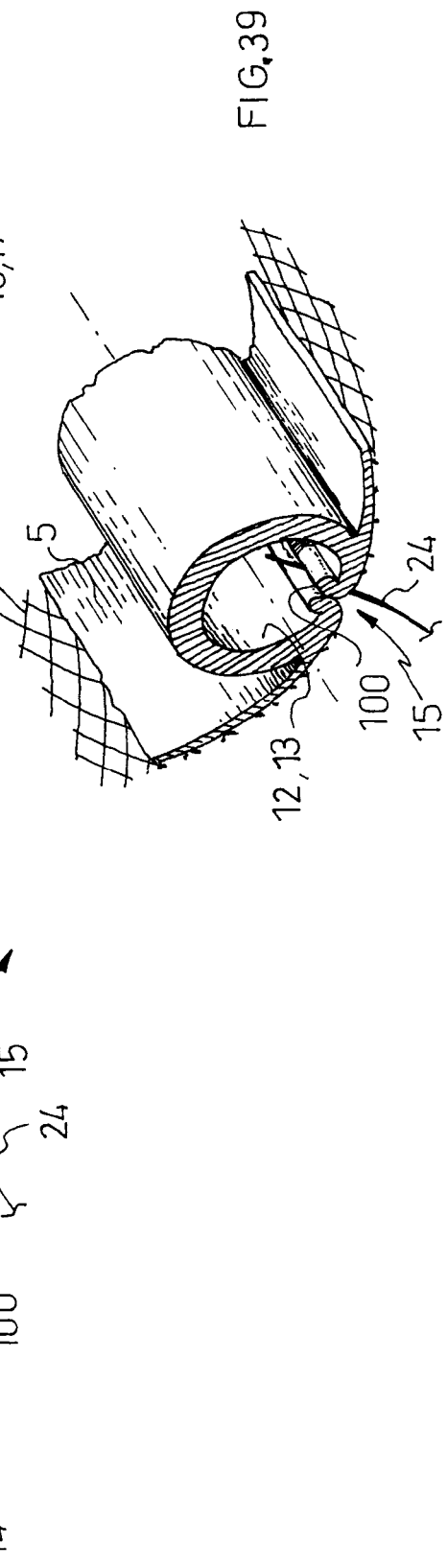

According to one embodiment, the side of the elongated body portion associated to the expansion means and free from said expanded active portion, or free side, is provided with a fissure 100 suitable for realizing a distal guidewire port 15 of the at least a guidewire lumen 12, 13. It is furthermore advantageous for said fissure 100 to be extended between the distal end and the proximal end of the elongated body portion associated to the expansion means 5 (FIGS. 37, 38 and 39).

Preferably, the side of the elongated body associated to the expansion means 5 and free from the expanded expansion means comprises a wall 105 that partially binds said at least a guidewire lumen 12,13. Said wall 105 is suitable for being bored by a guidewire end 106, for example the proximal end, in order to slip said guidewire 24 through the bored portion of the wall 105 (FIG. 40).

According to a further embodiment, the at least a guidewire lumen 12 and/or 13 of the tracking means has a plurality of distal guidewire ports 14, 15, $15^I, 15^{II}, 15^{III}, 15^{IV}$ and/or $15^V$, $15^{VI}, 15^{VII}, 15^{VIII}, 15^{IX}, 15^X, 15^{XI}$, $15^{XII}, 15^{XIII}, 15^{XIV}$, spaced out along said elongated body 2 (FIGS. 31, 32, 33, 34, 35 and 36).

Preferably, the guidewire tracking means 11 comprises a plurality of guidewire lumens 12, 13,$13^I,13^{II},13^{III}$ associated to each of said distal guidewire ports 14,15, $15^I,15^{II},15^{III},15^{IV}$ (FIGS. 31, 32).

Advantageously, the at least a guidewire lumen 12 and/or 13 has a distal guidewire port 14, or apical port, at the tip of said distal end portion 3 of the elongated body 2 (FIGS. 31, 32, 33, 34, 35 and 36).

With further advantage, a first guidewire lumen 12 associated to said apical port 14 is provided in the body and a second guidewire lumen 13 is associated to a plurality of distal guidewire ports 15, $15^I,15^{II},15^{III},15^{IV}$; $15^V,15^{VI},15^{VII},15^{VIII}$, $15^{IX},15^X,15^{XI},15^{XII},15^{XIII},15^{XIV}$ or side ports, provided on a side of the elongated body opposite the expansion means (FIGS. 35 and 36).

As an extremely advantageous alternative, a single guidewire lumen 12, 13 associated to said apical port 14 is provided in the body and is also associated to a plurality of distal guidewire ports 15, $15^I,15^{II},15^{III},15^{IV};15^V,15^{VI},15^{VII}$, $15^{VIII},15^{IX},15^X,15^{XI},15^{XII}$, $15^{XIII},15^{XIV}$, or side ports, provided on a side of the elongated body opposed to the expansion means (FIGS. 33 and 34).

In a further variation of the invention, the at least a guidewire lumen 13 has a distal guidewire port 15 near a distal end of the expansion means 5.

Advantageously, the at least a guidewire lumen 13 has at least a distal port 15, $15^I,15^{II},15^{III},15^{IV};15^V,15^{VI}, 15^{VII},15^{VIII}$, $15^{IX},15^X,15^{XI},15^{XII},15^{XIII},15^{XIV}$ in a portion of the elongated body 2 that lies between a distal end and a proximal end of the expansion means 5.

In a further variation of the invention, the endolumenal device can be advantageously used in order to improve maneuverability and clinical efficacy of some embolization containment devices (ECD) during coronary angioplasty and stenting.

Actually, a frequent complication of these procedures is the so called "no-flow phenomenon", consisting of impairment of the blood to flow down to the distal vessels, even though the obstruction has been removed.

This calamitous event is mainly caused by the distal embolization of the thrombus debris, and arterial spasms induced by some vaso-constrictive substances released into the blood stream because of the plaque crumbling and compression during balloon inflation.

These events are frequent when treating recent coronary occlusions in acute myocardial infarction, or when treating coronary lesions with angiographic evidence of a thrombus within the lumen, as in unstable angina.

Therefore, in addition to bifurcated lesion treatment, the proposed device will find large scale application in the situations as described here following.

Most ECD currently in use take the form of an occluding balloon 102 (FIG. 42b), or of a basket-shaped or an umbrella-shaped device 101 (FIG. 42c), which necessarily blocks the flow distally of debris, and substances which can cause vasospasms.

An example of such application is described with the following steps:

Step 1—a conventional guidewire (cGW) 24 is advanced beyond the occlusion as a "trailblazer" for the ECD 101. In fact, these devices have less maneuverability and are more fragile than cGW 24 and, therefore, can't be used to bore, and to cross an occlusive thrombus (FIG. 41).

Step 2—the ECD 101 is positioned as proximal as possible, but sufficiently distant to permit the entrapment of the embolic material and to allow easy handling and positioning of a stent-delivery system, and finally, stent deployment. Furthermore, positioning must be without excessive advancement of the ECD which would allow embolic material to escape into lateral branches 34, if positioned beyond vessel bifurcations.

Step 3—the ECD 101 is activated (i.e., the "umbrella" is opened or the "balloon" inflated), after which the cGW is withdrawn, in order to avoid its jailing between the stent and the vessel wall after stent deployment (FIG. 42a).

Step 4—a conventional stent-delivery system is advanced using the ECD 101 as a guidewire (FIG. 43).

Step 5—the stent-delivery system is inflated and the stent deployed (FIG. 44).

Step 6—debris and vasospastic substances, released during the stenting procedure, and entrapped by the ECD, are removed: with suction using a dedicated probe which has been advanced until it is contiguous with the occlusive "balloon", or withdrawn within the "umbrella", after its closure (FIG. 45).

As clearly described, this technique presents some drawbacks:

ECD 101, used as guidewire, give low support to the delivery systems especially when they are positioned very proximally;

a guidewire 24 repositioning could be needed after the stent deployment because of procedural complications (such as dissections) or in order to treat other lesions which come to light only after they has been re-opened. This procedure takes time and can be hazardous and unsuccessful.

Therefore, leaving the guidewire 24 for the duration of the procedure would be preferable.

All of this is easily performed with the proposed device 1 which allows to ride both a cGW 24 (represented with a broken line in FIGS. 43, 44 and 45) and a ECD 101 or 102 simultaneously, utilizing the apical port 14 and a lateral or side port 15 provided on a side of the elongated body of the expansion means 5 (FIGS. 35,36).

Therefore, we can leave a distally positioned cGW 24 for the duration of the procedure, as an "auxiliary wire" to give more support to the delivery system and to avoid re-crossing the stented lesion, should this become necessary.

Figure 46:
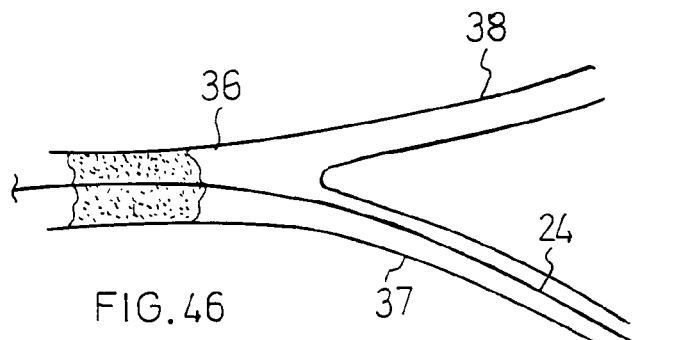
FIG. 46 to 51 show a cross portion through a bifurcation during six stages in the deploying of embolization containment devices and of an endolumenal prosthesis.
Figure 49:
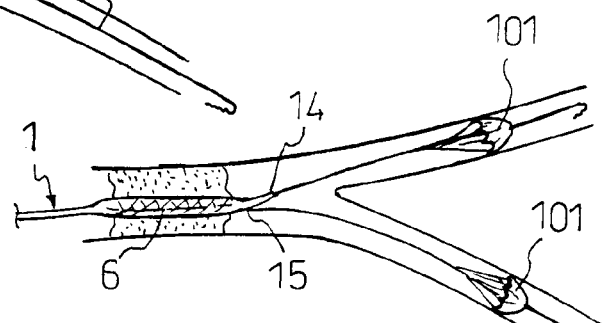
Figure 47:
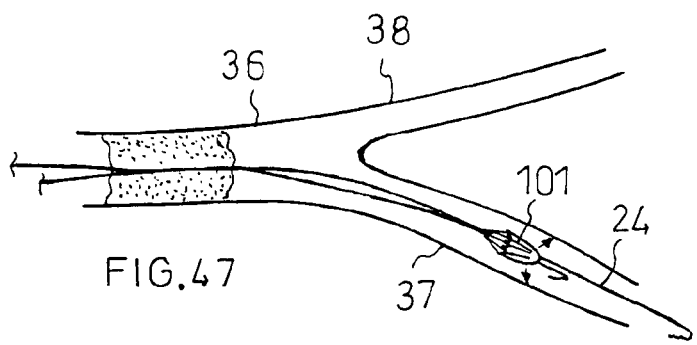
Figure 50:
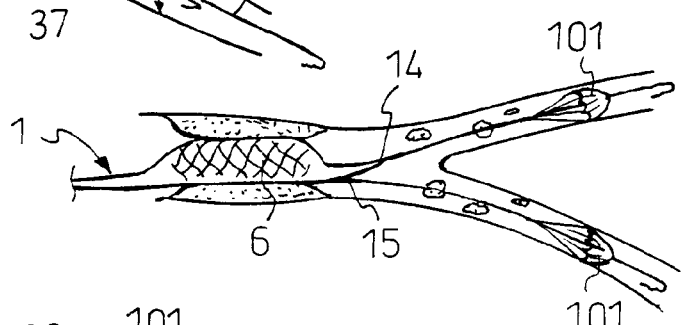
Figure 48:
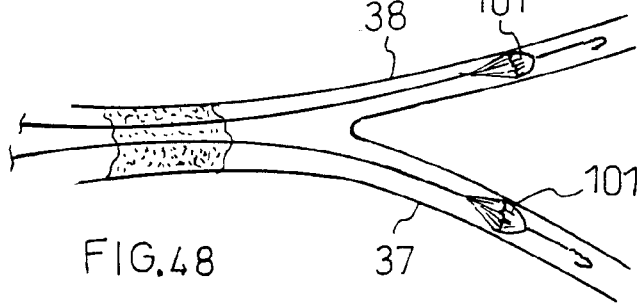
Figure 51:
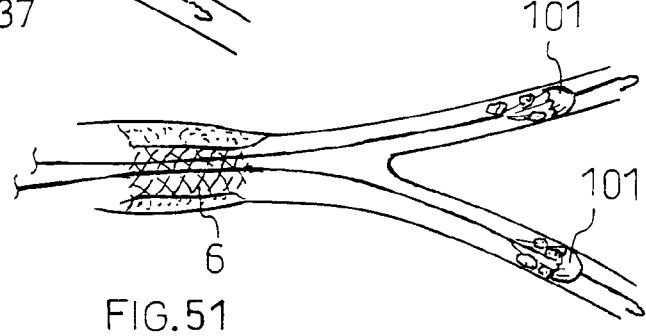
Figure 52:
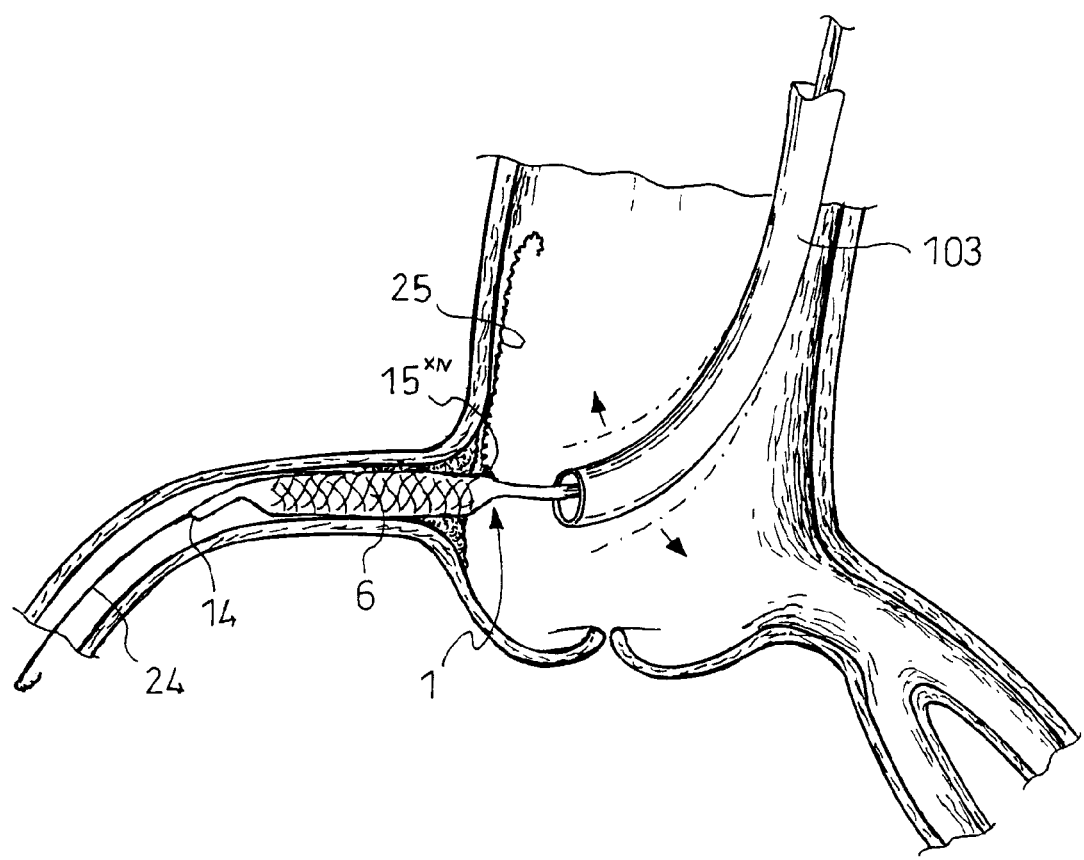
FIG. 52 shows a cross portion through the coronary ostium during a stage in the deploying of an endolumenal prosthesis.

This proposed device also offers a significant clinical advantage in the treatment of a thrombotic occlusion involving the ostium of a branch, or just proximal to a vessel bifurcation (very frequent cases), as shown in the following steps:

Step 1—the occlusion is crossed using a cGW 24 as a "trailblazer" (FIG. 46);

Step 2—a first ECD 101 is advanced into a first branch 37 (FIG. 47);

step 3—a second ECD 101 is advanced into a second branch 38, and both ECD are activated after the cGW 24 withdrawal (FIG. 48);

step 4—the proposed stent-delivery device 1 is advanced and positioned with the simultaneous use of both ECD's as guidewires (FIG. 49);

step 5—the stent is deployed and the vessel patency and the blood flow restored (FIG. 50);

step 6—the debris and any substance released during the procedure, entrapped by the 2 ECD's, are finally removed (FIG. 51).

Further clinical condition, where the device is extremely useful, is in an ostial lesion at the origin of the right coronary artery or a saphenous graft. In this case the engagement of a guidecatheter 103 is impossible due to the narrowing of the lumen. Therefore the guidecatheter 103 is positioned free in the middle of the aortic lumen, opposite the ostium, where there are a continual cardiac-cycle related movements of both the guidecatheter 103 and the delivery system 1.

In such circumstances the stent positioning and deployment, using the known devices, is necessarily imprecise and may improperly be implanted, or may be the cause of failure of the procedure. So, often times, these clinical situations are referred to surgeon for aorto-coronary bypass grafting.

Utilising the proposed device 1, it is possible to attain a precise positioning and deployment. The proposed method comprises: positioning of a first guidewire 24 in the diseased vessel suitable to fit it in the apical port 14 of a proposed device guidewire lumen; then positioning of a second guidewire 25 free in the aortic lumen and fitting said free guidewire in a proposed device side port $15^{XIV}$, just proximal to a stent 6 crimped down on the delivery system. In this way, the proposed device 1 can be advanced in the right coronary artery until the emerging second guidewire 25 blocks the delivery system with the proximal edge of the stent 6 perfectly aligned with the aortic wall. By maintaining a constant, even push until the stent delivery system (balloon) is activated (inflated), it is possible to attain a stable positioning within the ostial lesion and, therefore, the proper deployment of a stent.

A further method of employment of the proposed device is in the stenting of bifurcated lesions, where the proposed device 1 allows the operator to implant simultaneously two stents $6^{I}$ and $6^{II}$, perfectly flanked with their proximal edges on the same level, utilizing a known "V" or "kissing" technique.

After having positioned guidewires 24, 25 in the respective branches 37 and 38, a first guidewire 24 is fitted in a first device through its apical port 14.

Figure 53:
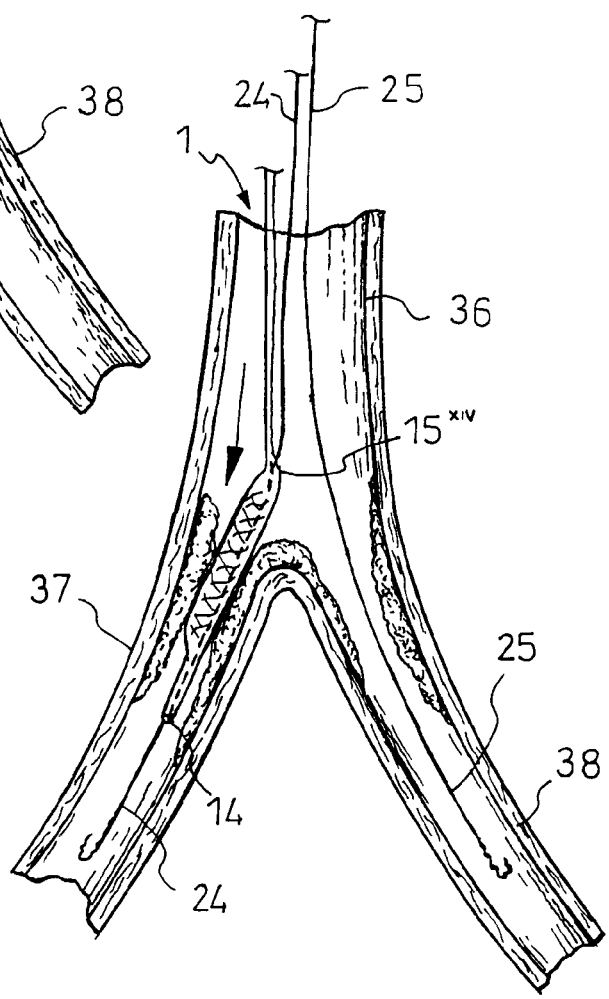

The same guidewire exits the device through a side port $15^{XIV}$, proximal to the stent, and the first device is then advanced in the first branch 37 (FIG. 53).

Figure 54:
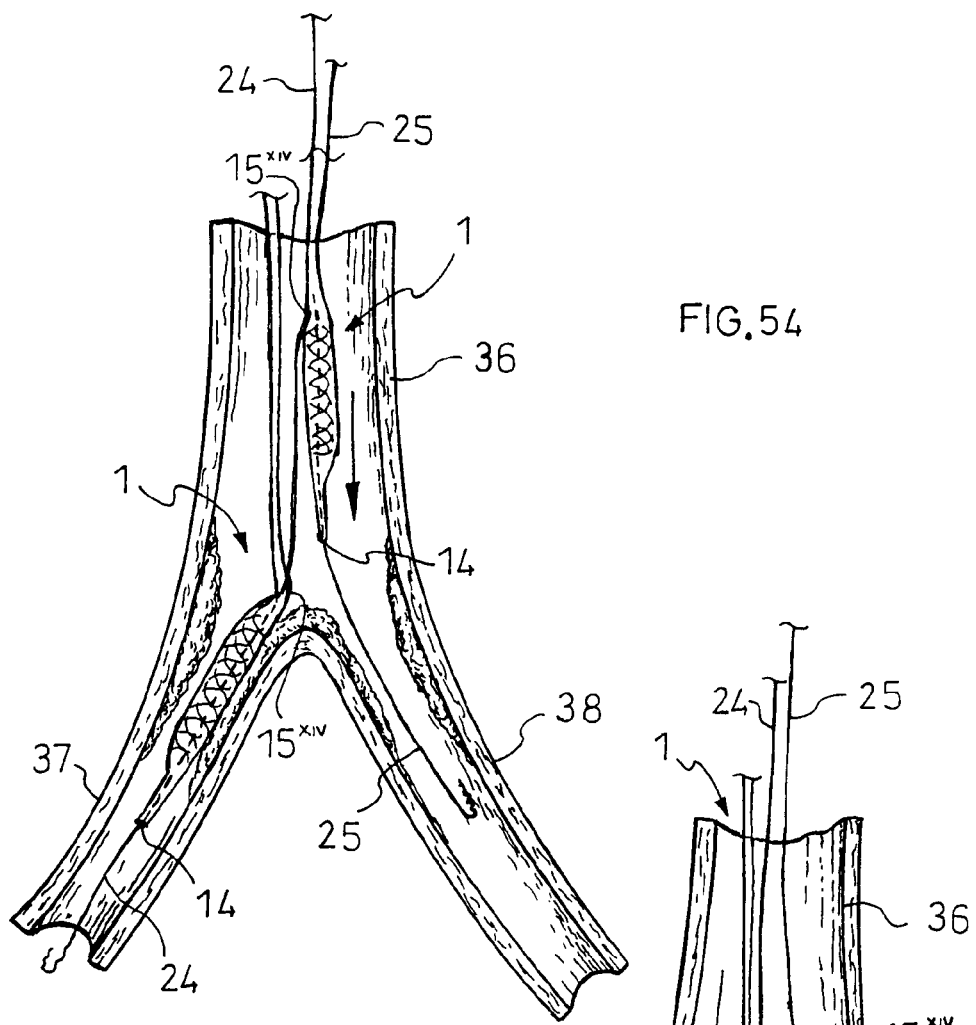
FIG. 53 to 55 show a cross portion through a bifurcation during three stages in the deploying of endolumenal prostheses by means of two endolumenal devices reciprocally connected through a guidewire.

A second guidewire 25 is received in a second device through its apical port 14. The first guidewire 24, received in the first device, is subsequently fitted in the second device through its side port $15^{XIV}$ proximal to the stent (FIG. 54).

This second device is then advanced until it is "automatically" blocked when its side port $15^{XIV}$ arrives at vessel bifurcation, where the two guidewires 24, 25 diverge. With a gentle pulling back of the first device, the respective side ports $15^{XIV}$ will be perfectly aligned and held in position by the first guidewire 24, which exits the first device and re-enters the second device.

Figure 55:
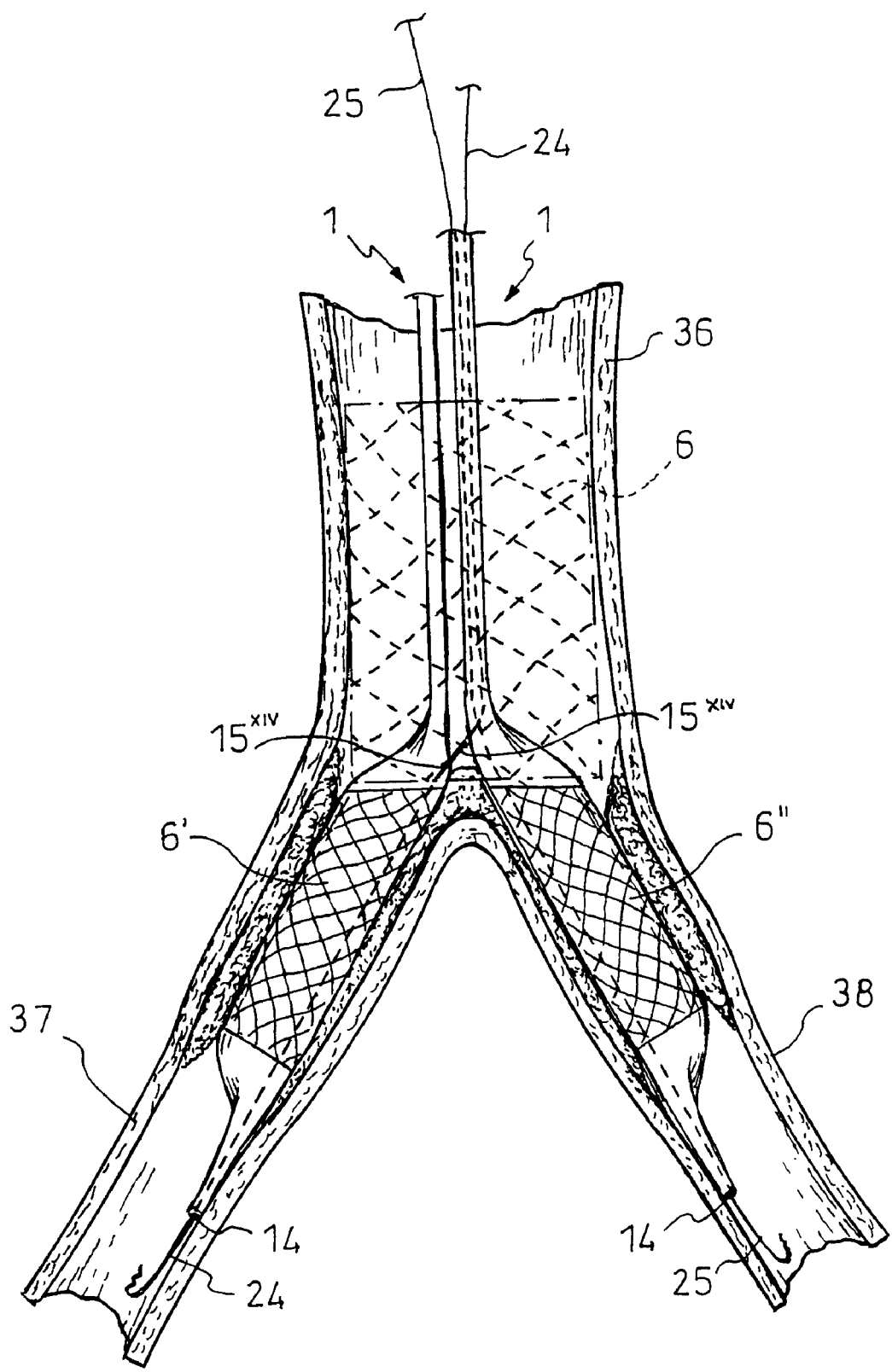
Figure 56:
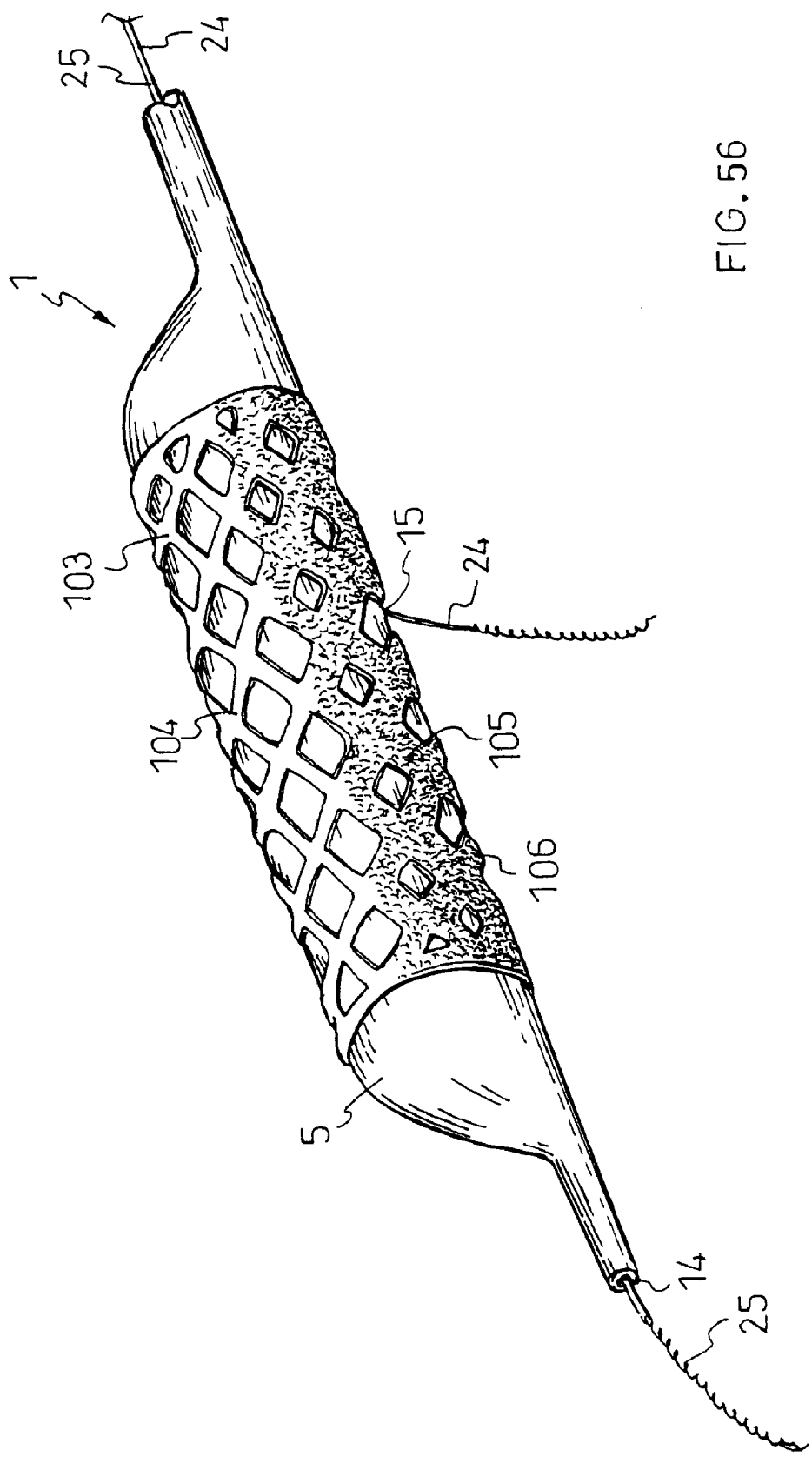
FIG. 56 shows a perspective view, partially sectioned, of an endolumenal device wearing a stent provided with a differentiated spatial behaviour.

In this way, the stents $6^I$ and $6^{II}$, mounted on two devices will necessarily be positioned with the proximal stent edges at the same level and with a complete coverage of the vascular "carina" between the two branches (FIG. 55).

Contrary to the "V" and "kissing" technique used with traditional balloons, the proposed device allows an "automatic" and precise positioning of paired stents, avoiding approximations, or that one of the two delivery systems is dislodged by the other during inflation of the balloons.

The proposed method of deployment is extremely efficient, particularly if employed subsequently a preliminary deployment of a stent 6 in the parent vessel, just proximal to the bifurcation; or implanting in the two branches dedicated stents having proximal-angled edges. In this way the coverage of the lesion is improved, avoiding overlapping of the stents, and with a complete coverage of the plaque (FIG. 55).

It is a further advantage that the proposed device has the possibility to rotate in a controlled manner along its longitudinal axis. In this way it is possible to properly orient and deploy stents. Thus, even without a bifurcated lesion, with a guidewire 24 previously deployed in a side-branch (i.e. in a septal or diagonal branch) it is possible to implant dedicated stents 103 with variable structures along their circumference (i.e.: struts 104, 105 of variable widths or with different drug coatings 106, and cells, with different diameter or dimensions, provided in different region of the stent) thereby allowing a specific treatment of selected areas in a single lesion.

A person skilled in the art could make numerous changes and adaptations to the preferred embodiment of the endolumenal device described above or substitute elements with others functionally equivalent, in order to meet contingent and specific requirements, without however departing from the scope of the following claims.

The invention claimed is:

1. Method for fitting a radially expandable prosthesis to the walls of branches of conduits forming a bifurcation, said bifurcation comprising a main conduit and a collateral conduit that branches off from a wall of the main conduit, comprising the following stages:
   providing a first endolumenal device and a second endolumenal device, the second endolumenal device comprising:
      an elongated body having a proximal end portion and a distal end portion;
      the distal end portion of said elongated body comprising an expansion device having a longitudinally extended active portion removably engageable with an endolumenal expandable prosthesis and adapted to adjust said prosthesis from a radially collapsed condition to a radially expanded condition;
      a guidewire tracking device at least partially extending along said elongated body, wherein
         said active portion of the expansion device is longitudinally associated to the elongated body in order to expand said prosthesis eccentrically from one side with respect to the elongated body, in order to leave free from said expanded active portion the other side of the elongated body, and
         said guidewire tracking device comprises at least a guidewire lumen at least partially extending inside said elongated body, having at least a guidewire distal port provided on a side of the elongated body opposed to the expansion device and suitable for slipping through it a guidewire portion of at least a guidewire placeable with its distal portion in said main or at least a secondary conduit;
   positioning a first guidewire in the main conduit so that it passes the bifurcation, and positioning a second guidewire in the collateral conduit, said guidewires being positioned in such a way as to follow an initial proximal section of path together and second distal sections of path that diverge at said bifurcation;
   fitting said first endolumenal device equipped with a radially expandable prosthesis onto a proximal end of the second guidewire, so that said second guidewire is received in a guidewire lumen of the endolumenal device through a distal guidewire port located on the tip of its elongated body;
   inserting said first endolumenal device into said conduits following the proximal and then the distal sections of path of the second guidewire in order to position the radially expandable prosthesis in the collateral conduit so that its proximal edge is positioned near a mouth of said collateral conduit;
   activating said expansion device so that said prosthesis is in its radially expanded condition and fixed by pressure to the wall of the collateral conduit;
   withdrawing said expansion device and the first endolumenal device from the second guidewire until it has been removed from the conduits;
   fitting said second endolumenal device equipped with a radially expandable prosthesis onto a proximal end of the first guidewire so that said first guidewire is received in a guidewire lumen through a distal guidewire port located on the tip of the second endolumenal device;
   fitting said second endolumenal device onto a proximal end of the second guidewire so that said second guidewire is received in the guidewire lumen through a distal guidewire port located on the portion of the elongated body that lies between a distal and a proximal end of the expansion device;
   inserting said second endolumenal device into the main conduit and slid along the proximal section of path of the guidewires until a distal portion of the second endolumenal device, located between the tip of said second endolumenal device and the distal guidewire port of the second guidewire lumen, is positioned beyond the bifurcation;
   activating the expandable device of said second endolumenal device so as to bring said prosthesis into its radially expanded condition and fixed by pressure to the wall of the main conduit and straddling the bifurcation;
   withdrawing said expansion device and then withdrawing the second endolumenal device from the guidewires until it has been removed from the conduits.

2. Method for fitting radially expandable prostheses to the walls of branches of conduits forming a bifurcation, said bifurcation comprising a proximal main conduit and a first and a second distal, secondary conduits which branch off from a distal end of the main conduit, forming between them a carina, comprising the following stages:

provides a first endolumenal device comprising:

an elongated body having a proximal end portion and a distal end portion;

the distal end portion of said elongated body comprising an expansion device having a longitudinally extended active portion removably engageable with an endolumenal expandable prosthesis and adapted to adjust said prosthesis from a radially collapsed condition to a radially expanded condition;

a guidewire tracking device at least partially extending along said elongated body, wherein said active portion of the expansion device is longitudinally associated to the elongated body in order to expand said prosthesis eccentrically from one side with respect to the elongated body, in order to leave free from said expanded active portion the other side of the elongated body, and said guidewire tracking device comprises at least a guidewire lumen at least partially extending inside said elongated body, having at least a guidewire distal port provided on a side of the elongated body opposed to the expansion device and suitable for slipping through it a guidewire portion of at least a guidewire placeable with its distal portion in said main or at least a secondary conduit;

positioning, through the main conduit, a first guidewire in the first secondary conduit and a second guidewire is positioned in the second secondary conduit, said guidewires being positioned so as to follow a first proximal section of path together and second distal sections of path that diverge after said bifurcation;

fitting said first endolumenal device equipped with a radially expandable prosthesis onto a distal end of the first guidewire, so that said first guidewire is received in a guidewire lumen of the endolumenal device through a distal guidewire port located at the tip of its elongated body;

fitting said first endolumenal device onto a proximal end of the second guidewire so that said second guidewire is received in the guidewire lumen through a distal guidewire port located near the distal end of the expansion device;

inserting said first endolumenal device into said conduits following the proximal section of path until the carina is positioned against the elongated body and near the distal guidewire port positioned near the distal end of the expansion device;

activating said expansion device so as to bring said prosthesis into its radially expanded condition, fixed by pressure to the wall of the main conduit;

withdrawing said expansion device and then withdrawing the first endolumenal device from the guidewires.

* * * * *